(12) United States Patent
Zhang et al.

(10) Patent No.: US 8,680,361 B2
(45) Date of Patent: Mar. 25, 2014

(54) LAMINATES WITH MICRO-TEXTURE

(75) Inventors: John Jianbin Zhang, Cincinnati, OH (US); Andrea Marie Breitenbach, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 389 days.

(21) Appl. No.: 12/837,735

(22) Filed: Jul. 16, 2010

(65) Prior Publication Data

US 2011/0015605 A1 Jan. 20, 2011

Related U.S. Application Data

(60) Provisional application No. 61/226,412, filed on Jul. 17, 2009.

(51) Int. Cl.
*A61F 13/15* (2006.01)

(52) U.S. Cl.
USPC ...... 604/367; 604/373; 604/372; 604/385.22; 604/385.29; 604/385.27; 604/385.24

(58) Field of Classification Search
USPC ............... 604/367, 373, 372, 385.22, 385.29, 604/385.27, 385.24
See application file for complete search history.

(56) References Cited

U.S. PATENT DOCUMENTS

| | | | |
|---|---|---|---|
| 4,446,189 A | 5/1984 | Romanek | |
| 5,683,787 A | 11/1997 | Boich et al. | |
| 2003/0183316 A1 | 10/2003 | Hamulski | |
| 2004/0222553 A1* | 11/2004 | Desai et al. | 264/171.24 |
| 2006/0131783 A1 | 6/2006 | Morman et al. | |

FOREIGN PATENT DOCUMENTS

| | | |
|---|---|---|
| JP | 10-000712 A | 1/1998 |
| JP | 2006-027089 A | 2/2006 |

OTHER PUBLICATIONS

PCT International Search Report, PCT/US2010/042266 date of mailing Sep. 20, 2010.

* cited by examiner

*Primary Examiner* — Jacqueline F. Stephens
(74) *Attorney, Agent, or Firm* — Christian M. Best; Charles R. Ware

(57) ABSTRACT

A laminate with micro-texture having attachment lines oriented in a primary direction and mechanically activated in the primary direction.

39 Claims, 23 Drawing Sheets

LAMINATES WITH MICRO-TEXTURE

CROSS REFERENCE TO RELATED APPLICATIONS

This application claims the benefit of U.S. provisional patent application 61/226,412 filed Jul. 17, 2009, the substance of which is hereby incorporated by reference.

FIELD

In general, embodiments of the present disclosure relate to laminates. In particular, embodiments of the present disclosure relate to activated laminates with micro-texture for use with absorbent articles.

BACKGROUND

Absorbent articles can absorb liquid bodily exudates such as sweat, blood, urine, menses, etc. An absorbent article can include elastic materials. Unfortunately, some elastic materials may have a rough plastic appearance or feel. Some integral elastic materials may not appear finished and garment-like. And some elastic materials tend to use materials inefficiently. Also some elastic materials may not adequately conform the article to a wearer's body. Absorbent articles with such elastic materials may look unattractive, cost more, and perform poorly.

DETAILED DESCRIPTION

The embodiments of laminate with micro-texture of the present disclosure can be used with all kinds of absorbent articles and disposable garments. An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

The embodiments of laminates with micro-texture of the present disclosure can be used in a front waistband, back waistband, leg band, ear, side panel, topsheet, anchoring band, extensible outer cover, and/or other suitable portions of a wearable absorbent article, as described herein. Such laminates can be attached to a wearable absorbent article as sheets, discrete pieces, or continuous bands, on the wearer side, on the garment side, or interposed between layers of the article (e.g. integral). The laminate can be attached in any manner known in the art, such as adhesive attachment, pressure bonding, thermal bonding, ultrasonic bonding, and the like, or combinations of any of these.

The figures of the present disclosure are intended to illustrate elements, their parts, and their relationships, as described in the specification; the figures are not intended to illustrate any particular relative or absolute size or dimension, unless otherwise stated in the text.

Figure 1A:
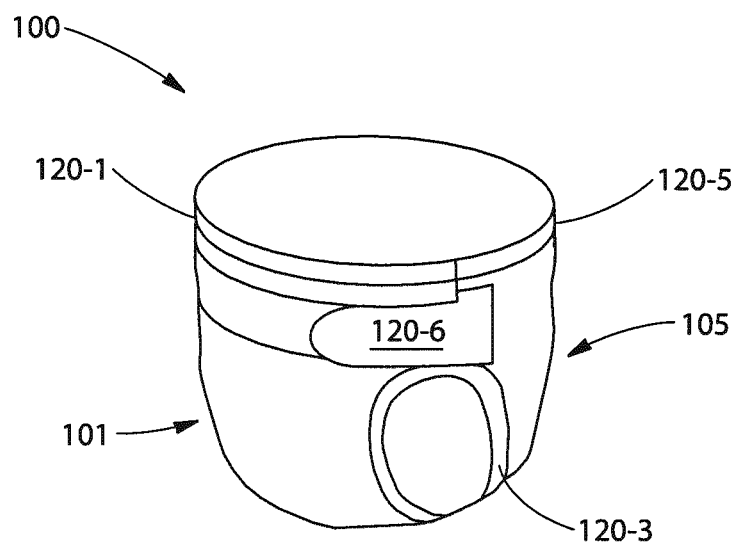
FIG. 1A illustrates a front outside perspective view of a front-fastenable wearable absorbent article formed for wearing, wherein the article includes laminates with micro-texture of the present disclosure.

FIG. 1A illustrates a front outside perspective view of a front-fastenable wearable absorbent article 100 formed for wearing. The article 100 has a front 101 and a back 105. The article includes a front waistband 120-1, legbands 120-3, a back waistband 120-5, and side ears 120-6. Any of the front waistband 120-1, legbands 120-3, back waistband 120-5, and side ears 120-6, or a portion thereof, can be configured to include or be formed from any of the embodiments of the laminates with micro-texture of the present disclosure.

While the present disclosure refers to front-fastenable absorbent articles, the present disclosure also contemplates alternate embodiments of absorbent articles using laminates, as described herein, wherein the absorbent articles are rear-fastenable or side fastenable. Thus, each embodiment of an absorbent article of the present disclosure that is described as front-fastenable can also be configured to be rear fastenable or side-fastenable, as will be understood by one of ordinary skill in the art.

Figure 1B:
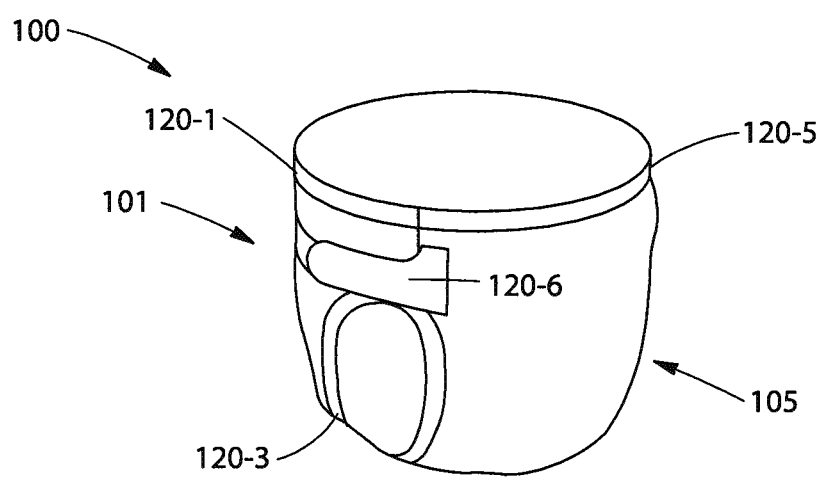
FIG. 1B illustrates a back outside perspective view of the article of FIG. 1A.

FIG. 1B illustrates a back outside perspective view of the article of FIG. 1A.

Figure 2A:
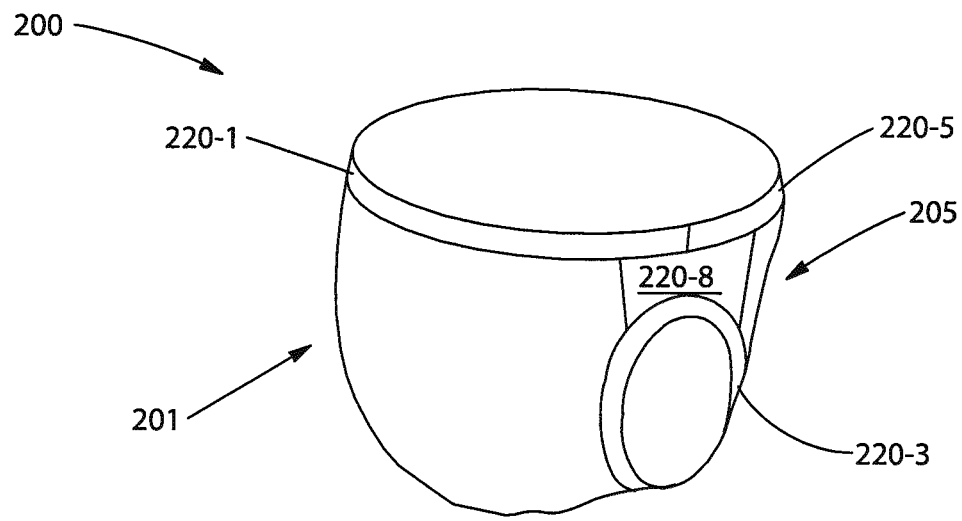
FIG. 2A illustrates a front outside perspective view of a pant-type wearable absorbent article formed for wearing, wherein the wherein the article includes laminates with micro-texture of the present disclosure.

FIG. 2A illustrates a back outside perspective view of a pant-type wearable absorbent article 200 formed for wearing. The article 200 has a front 201 and a back 205. The article includes a front waistband 220-1, legbands 220-3, a back waistband 220-5, and side panels 220-8. Any of the front waistband 220-1, legbands 220-3, back waistband 220-5, and side panels 220-8 can be configured to include or be formed from any of the embodiments of the laminates with micro-texture of the present disclosure.

Throughout the present disclosure, a reference to a pant-type wearable absorbent article refers to an article with sufficient stretch to enable it to be readily pulled over a wearer's hips and buttocks while the waist and leg openings are formed. A pant-type wearable absorbent article can refer to an embodiment that is side-fastenable, to an embodiment that is front-fastenable, to an embodiment that is rear-fastenable, or to an embodiment without fasteners. A reference to a pant-type wearable absorbent article can also refer to an article with preformed waist and/or leg openings or to an embodiment that is not preformed. Thus, each embodiment of an absorbent article of the present disclosure that is described as pant-type can be configured in any of these ways, as will be understood by one of ordinary skill in the art.

Figure 2B:
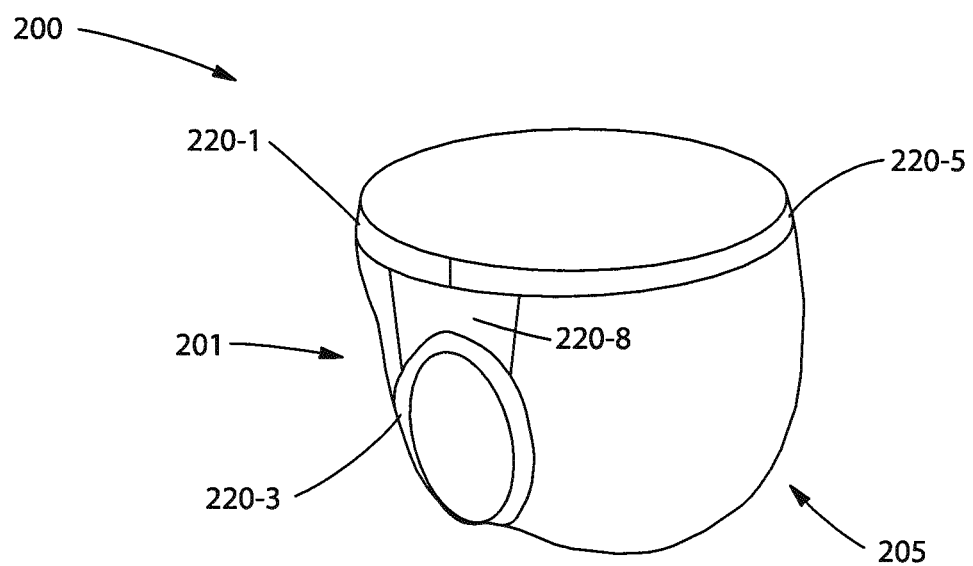
FIG. 2B illustrates a back outside perspective view of the article of FIG. 2A.

FIG. 2B illustrates a back outside perspective view of the article of FIG. 2A.

Figure 3A:
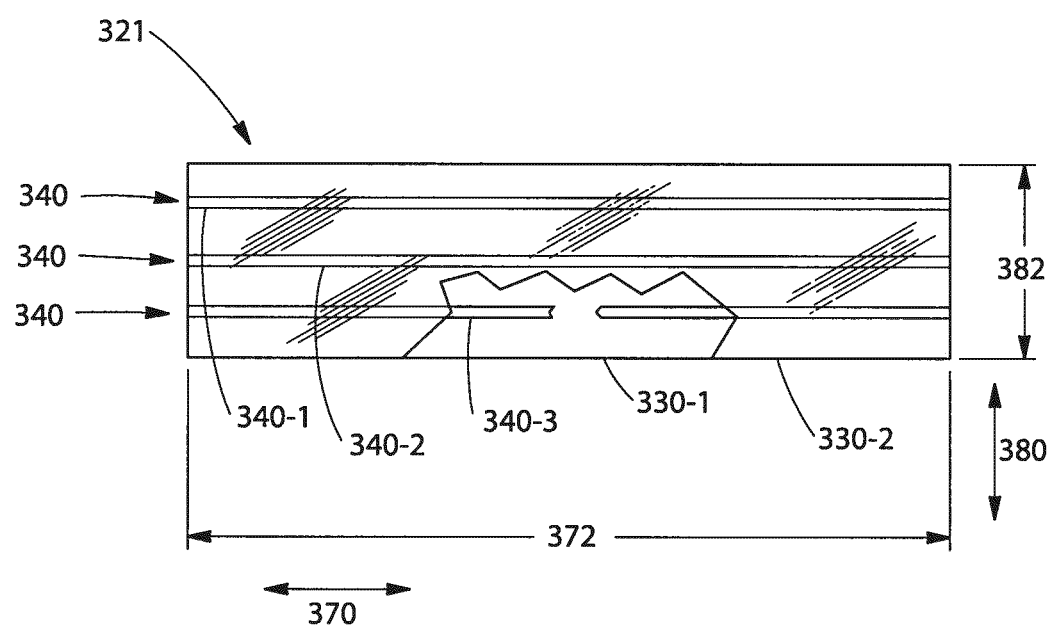
FIG. 3A illustrates a top view of a two-layer intermediate laminate of the present disclosure, before activation.

FIG. 3A illustrates a top view of an intermediate laminate 321 before being mechanically activated by incremental stretching. For reference, the intermediate laminate 321 includes a primary direction 370 and a secondary direction 380. The secondary direction 380 is perpendicular to the primary direction 370.

The intermediate laminate 321 has a first layer 330-1 and a second layer 330-2. The first layer 330-1 is disposed subjacent to the second layer 330-2. The intermediate laminate 321 also includes a plurality of first attachment lines 340. The first attachment lines 340 include a first line 340-1, a second line 340-2, and a third line 340-3. The first attachment lines 340 are disposed between the first layer 330-1 and the second layer 330-2. The second layer 330-2 is illustrated as semi-transparent, so the first attachment lines 340 are visible through the second layer 330-2. For purposes of illustration, a portion of the second layer 330-2 and a portion of the third line 340-3 are shown broken away.

The intermediate laminate 321 is in the form of a sheet-like band and has an overall length 372 in a longitudinal direction, which is parallel with the primary direction 370, and an overall initial width 382 in the secondary direction 380. In the embodiment of FIG. 3A, the overall length 372 is much greater than the overall initial width 382, resulting in the intermediate laminate 321 with an overall rectangular shape; however this is not required and the intermediate laminate 321 can be configured in various other shapes, e.g., via curving the laminate on an article or folding or cutting it to shape it.

In various embodiments, the overall initial width 382 can have various dimensions. For example, the intermediate laminate 321 can have an overall width 382 that is less than or equal to 50 millimeters, less than or equal to 40 millimeters, less than or equal to 30 millimeters, less than or equal to 20 millimeters, less than or equal to 15 millimeters, less than or equal to 10 millimeters, or less than or equal to any integer value from 0 to 50 millimeters.

In an alternate embodiment, the intermediate laminate 321 can be configured such that the primary direction 370 is angled with respect to the longitudinal direction of the intermediate laminate 321. For example, the primary direction 370 can be angled within 45 degrees, 30 degrees, 15 degrees, or substantially parallel with the longitudinal direction, or at any other angle.

The first layer 330-1 has, in the primary direction 370, a first extensibility and a first elasticity with a first set. The second layer 330-2 has, in the primary direction 370, a second extensibility and a second elasticity with a second set.

As used herein, the term "extensibility" refers to the ability of a material to elongate to a given percentage, without substantial rupture or breakage. Micro-sized rupture or breakage of a material is not considered substantial rupture or breakage. However, macro-sized ruptures through the structure (e.g. one or more large tears such as tears greater than about 5 millimeters in any direction, or breaking into two or more pieces, or resulting in significant structural degradation which may render the material unusable for its intended purpose) are considered substantial ruptures or breakage.

In various embodiments, the first layer 330-1 can have a first extensibility that is greater than or equal to 50%, greater than or equal to 100%, greater than or equal to 200%, greater than or equal to 350%, greater than or equal to 500%, or any integer value for percent from 0% to 500%. In some embodiments, the second layer 330-2 can have a second extensibility that is greater than or equal to 50%, greater than or equal to 100%, greater than or equal to 200%, greater than or equal to 350%, greater than or equal to 500%, or greater than any integer value for percent from 0% to 500%.

In the embodiment of FIG. 3A, the second set of the second layer 330-2 is greater than the first set of the first layer 330-1. In various embodiments, the second layer 330-2 can have a second set that is greater than or equal to 50%, greater than or equal to 60%, greater than or equal to 70%, greater than or equal to 80%, greater than or equal to 90%, equal to about 100%, or greater than any integer value for percent from 50% to 100%, when the set is measured by using the Hysteresis Test method, as described herein.

The first layer 330-1 and/or the second layer 330-2 can include or be formed by one or more of various kinds of materials, such as nonwovens, films, foams, coextruded skin/monolayers, laminates, and combinations thereof. The first layer 330-1 and/or the second layer 330-2 can include or be formed by one or more sheets of material. In a first exemplary embodiment, the first layer 330-1 can be a sheet of film having elastic properties and the second layer 330-2 can be a sheet of film having plastic properties. In a second exemplary embodiment, the first layer 330-1 can be a sheet of film having elastic properties and the second layer 330-2 can be a sheet of nonwoven laminated to a film having plastic properties. In various embodiments, the outer surface of the first layer 330-1 and/or the second layer 330-2 can be treated by various methods to improve its surface properties, such as softness.

Additionally, the first layer 330-1 can include or be formed by one or more bands of material, strands of material, and combinations thereof. The first layer 330-1 can include or be formed by one or more compositions of materials, such as thermoplastic elastomers, styrenic block copolymers, styrene ethylbutylene styrene, styrene ethylene propylene styrene, styrene ethylene ethylene propylene styrene, styrene butadiene styrene, styrene isoprene styrene, polyolefin elastomers, polyurethanes, polyesters, rubbers, Vistamaxx™ from Exxon-Mobil, Versify™ from Dow, Adflex™ from Lyondell-Basell, and combinations thereof. The second layer 330-2 can include or be formed by one or more compositions of materials, such as polyethylenes (e.g. LDPEs and LLDPEs), polypropylenes, copolymers, polyolefins, filled polyolefins, polyesters, and combinations thereof. The first layer 330-1 and/or the second layer 330-2 can have a basis weight that is less than or equal to 500 grams per square meter (gsm), less than or equal to 200 gsm, less than or equal to 100 gsm, or any integer value for gsm within any of these ranges.

Part, parts, substantially all, or all of the first layer 330-1 and/or the second layer 330-2 can be liquid impermeable or liquid permeable. The first layer 330-1 and/or the second layer 330-2 can be vapor impermeable or vapor permeable. In various embodiments, either or both of the layers can be permeable by their construction, or rendered permeable by aperturing.

The first layer 330-1 is attached to the second layer 330-2 by a first attachment area. In various embodiments, greater than 50%, at least 60%, at least 70%, at least 80%, at least 90%, substantially all, or all of the first attachment area is formed by the first attachment lines 340. Also in various embodiments, the first attachment lines 340 can form any integer value for percent from 50% to 100% of the first attachment area.

Each of the first attachment lines 340 is oriented in a direction of orientation that is parallel with each other, however, in some embodiments, this is not required. Each of the first attachment lines 340 is also oriented in a direction of orientation that is parallel with the primary direction 370, however, in some embodiments, this is also not required.

Each of the first attachment lines 340 is a continuous straight line. However, in various embodiments, part, or parts, or substantially all, or all of one or more of the first attachment lines 340 can include a continuous line, or a substantially continuous line, or a discontinuous line, or a series of line segments, or a series of dashes, a series of dots, or combinations of any of these. Also, in various embodiments, part, or parts, or substantially all, or all of one or more of the first attachment lines 340 can be curved, segmented, or patterned. Any of the first attachment lines 340 can be any kind of attachment, such as a line of embossment, a line of thermal bonding, a line of ultrasonic bonding, a line of adhesive, etc. For example, a line of adhesive could be formed from adhesives H2031, H2861, or H2988F available from Bostik, Inc. of Wauwatosa, Wis., or from adhesive 526 available from National Adhesives of Bridgewater, N.J. Without wishing to be bound by the theory, it is believed that the adhesive should be sufficiently flowable to survive a mechanical activation process while still adhering to the layers to which it is attached.

The first layer 330-1 is attached to the second layer 330-2 by an attachment with an overall peel strength. In various embodiments, greater than 50%, at least 60%, at least 70%, at least 80%, at least 90%, substantially all, or all of the overall peel strength is provided by the first attachment lines 340. Also in various embodiments, the first attachment lines 340 can provide any integer value for percent from 50% to 100% of the overall peel strength of the attachment. As an example, while the first layer 330-1 may be continuously attached to the second layer 330-2, greater than 50%, at least 60%, at least 70%, at least 80%, at least 90%, substantially all, or all of the overall peel strength can be provided by the first attachment lines 340, with the balance of the overall peel strength provided by areas outside of the first attachment lines 340.

In the embodiment of FIG. 3A, the first layer 330-1 and the second layer 330-2 are each relaxed when they are attached to each other. However, in various embodiments, the first layer 330-1 can be prestrained to various relative prestrains as it is attached to the second layer 330-2. As examples, the first layer 330-1 can be attached to the second layer 330-2 at a relative prestrain that is greater than or equal to 500%, greater than or equal to 350%, greater than or equal to 200%, greater than or equal to 100%, greater than or equal to 50%, or greater than or equal to any integer value for percent from 50% to 500%. As further examples, the first layer 330-1 can be attached to the second layer 330-2 at a relative prestrain that is less than or equal to 20%, less than or equal to 15%, less than or equal to 10%, less than or equal to 5%, about zero, equal to zero, or less than or equal to any integer value for percent from 20% to 0%.

In an exemplary embodiment, the second layer 330-2 can be a sheet of film with plastic properties that is attached to a first side the first layer 330-1, as described above, while the first layer 330-1 can be a laminate with overall elastic properties, wherein the laminate is formed from a sheet of film with elastic properties on the first side and a sheet of film with plastic properties on the opposite side. In variations of this exemplary embodiment, the elastic film can comprise at least 50%, at least 60%, at least 70%, at least 80%, or more of the total thickness of the first layer 330-1. In this exemplary embodiment, the plastic properties on the opposite side of the first layer 330-1 can help balance out the effects of the plastic properties of the second layer 330-2, resulting in an intermediate laminate 321 that tends to lie flat.

Once the first layer 330-1 is attached to the second layer 330-2, as described above, the intermediate laminate 321 is formed. The intermediate laminate can then be mechanically activated to form the activated laminate 322 of FIG. 3B.

Figure 3B:
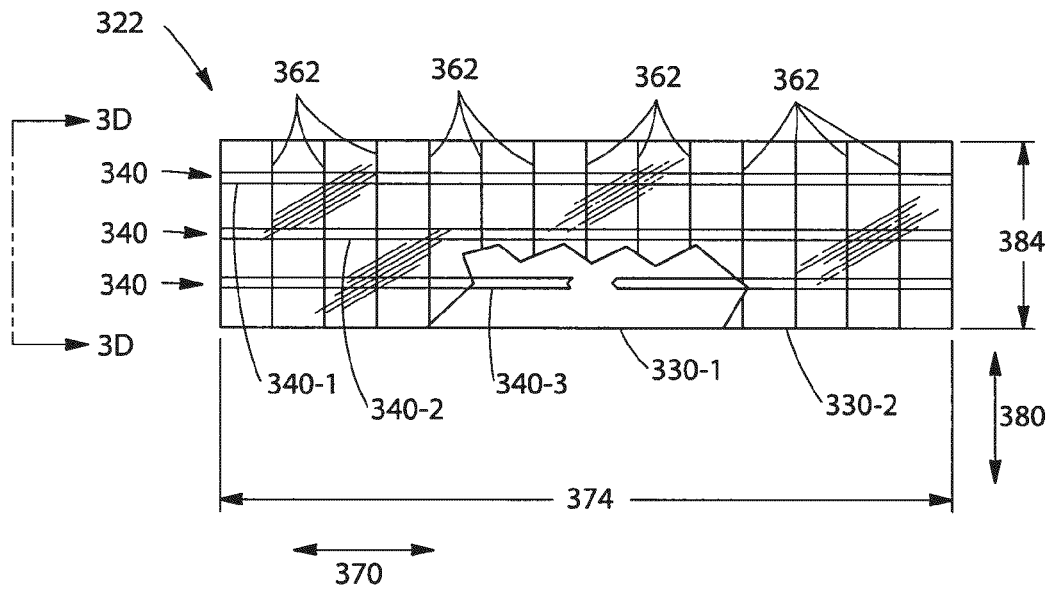
FIG. 3B illustrates a top view of the laminate of FIG. 3A, after activation, in a flat state.

FIG. 3B illustrates a top view of an activated laminate 322, which is the intermediate laminate 321 after being mechanically activated by incremental stretching. As a result, in the activated laminate 322, the second layer 330-2 has been set. In FIG. 3A, the activated laminate 321 is illustrated in an extended state, as if pulled flat to remove all contraction.

The activation can be accomplished in various ways, such as by extending the intermediate laminate 321 in the primary direction 370, stretching the intermediate laminate 321 between several pairs of nip rolls with each pair running at a higher speed compared to the previous one, incrementally stretching the intermediate laminate 321, or other activation techniques, such as ring-rolling. The activation process can be applied to the intermediate laminate 321 in a relaxed state or under a process tension. It is contemplated that the activation process can be applied to the intermediate laminate 321 before it is attached to an article or after it is attached to the article. In various embodiments, the activation can be accomplished using a profiled activation process, such as those described in US patent application entitled "Process for Activating a Web", filed Nov. 19, 2007 and published as US publication 20090127742. In various embodiments, the activation can be applied in a direction that is angled with respect to the primary direction. For example, the actication can be applied in a direction that is at an angle of 45 degrees, 30 degrees, or 15 degrees with respect to the primary direction, or at any other angle. It is contemplated that the activation process can be applied at various temperatures.

In the embodiment of FIG. 3A, the activated laminate 322 is illustrated as including a plurality of tooth marks 362 from an intermeshing of teeth in an activation process. As an example, the inelastic extension can be accomplished with intermeshing teeth having 0.100" pitch, with a 5.27 millimeter depth of engagement. In various embodiments, during the activation process, the intermediate laminate 321 can be extended, in the primary direction 370, at least 20%, at least 50%, at least 100%, at least 150%, at least 200%, at least 250%, at least 300%, at least 350%, at least 400%, at least 450%, at least 500%, or any integer value for percent from 50% to 500%. The activated laminate 322 may or may not be activated in the secondary direction 380, or any other direction, before or after attachment to an article. The activated laminate 321 has an overall extended length 374, measured in the primary direction 370, and an overall extended width 384, measured in the secondary direction 380. The overall extended width 384 is similar to the overall initial width 382, or slightly less due to due to neckdown and/or plastic deformation from the activation process.

The activated laminate 322 has, in the primary direction 370, a laminate extensibility. In various embodiments, the activated laminate 322 can have a laminate extensibility that is greater than or equal to 10%, greater than or equal to 20%, greater than or equal to 35%, greater than or equal to 50%, greater than or equal to 100%, greater than or equal to 200%, greater than or equal to 350%, greater than or equal to 500%, or any integer value for percent from 0% to 500%.

The activated laminate 322 has, in the primary direction 370, a laminate set. In various embodiments, the activated laminate 322 can have a laminate set that is less than or equal to 50%, less than or equal to 35%, less than or equal to 20%, less than or equal to 15%, less than or equal to 10%, less than or equal to 5%, or less than or equal to any integer value for percent from 50% to 0%, when the set is measured by using the Hysteresis Test method, as described herein.

Figure 3C:
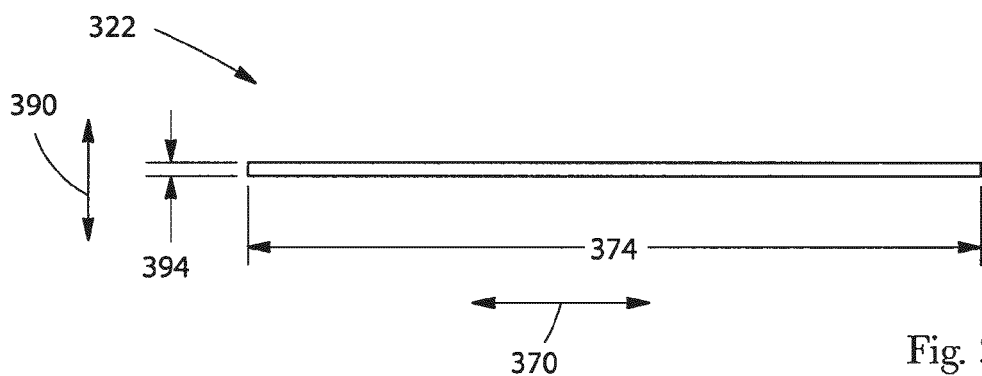
FIG. 3C illustrates a side view of the activated laminate of FIG. 3B.

FIG. 3C illustrates a side view of the activated laminate 322 of FIG. 3B. The activated laminate 322 has an overall thickness 394 in the extended state. The overall thickness 394 is measured in a tertiary direction that is perpendicular to the primary direction 370 and perpendicular to the secondary direction 380.

Figure 3D:
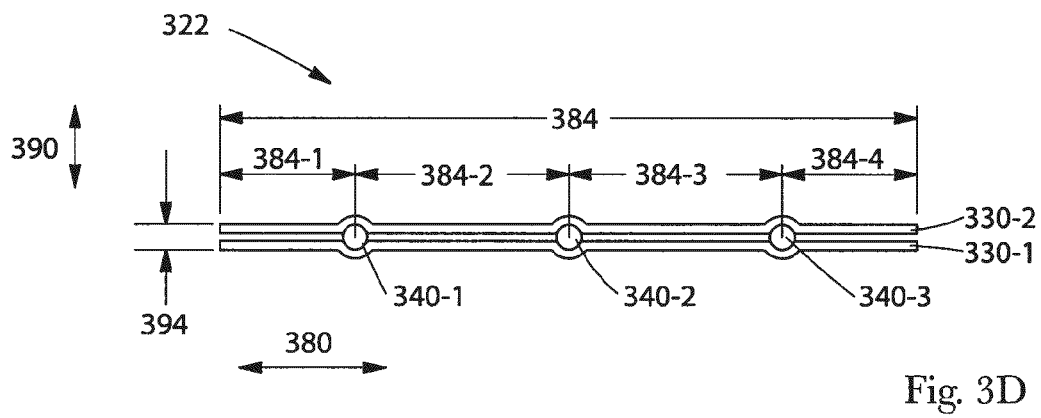
FIG. 3D illustrates an end view of the activated laminate of FIG. 3B.

FIG. 3D illustrates an end view of the activated laminate 322 of FIG. 3B. While the activated laminate 322 includes three first attachment lines 340, in various embodiments, the activated laminate 322 can include one, two, three, four, five, six, seven, eight, nine, ten, or more attachment lines.

The first line 340-1 is spaced apart from the left edge of the activated laminate 322 by a first distance 384-1, measured in the secondary direction 380 from the left edge to the center of the first line 340-1. The second line 340-2 is spaced apart from the first line 340-1 by a second distance 384-2, measured in the secondary direction 380 from the center of the first line 340-1 to the center of the second line 340-2. The third line 340-3 is spaced apart from the second line 340-2 by a third distance 384-3, measured in the secondary direction 380 from the center of the second line 340-2 to the center of the third line 340-3. The third line 340-3 is also spaced apart from the right edge of the activated laminate 322 by a fourth distance 384-4, measured in the secondary direction 380 from the center of the third line 340-3 to the right edge.

In various embodiments, the first attachment lines 340 can have substantially uniform or uniform spacing. For example, in the activated laminate 322, the second distance 384-2 and the third distance 384-3 can be substantially equal or equal.

Adjacent lines in the first attachment lines 340 can be spaced apart by various distances. As examples, adjacent lines in the first attachment lines 340 can be spaced apart by a distance that is greater than or equal to 0.5 millimeters, greater than or equal to one millimeter, greater than or equal to two millimeters, greater than or equal to four millimeters, greater than or equal to six millimeters, greater than or equal to eight millimeters, greater than or equal to ten millimeters, greater than or equal to twelve millimeters, greater than or equal to fifteen millimeters, greater than or equal to twenty millimeters, greater than or equal to twenty five millimeters, or greater than or equal to thirty millimeters.

Any of the lines in the first attachment lines 340 can have various line widths, measured across the cross-section of the line, in the secondary direction 380. As examples, an attachment line can have a line width that is less than or equal to five millimeters, less than or equal to three and a half millimeters, less than or equal to two millimeters, less than or equal to one millimeter, less than or equal to 0.8 millimeters, less than or equal to 0.6 millimeters, less than or equal to 0.4 millimeters, less than or equal to 0.2 millimeters, or less than or equal to 0.1 millimeters.

Figure 3E:
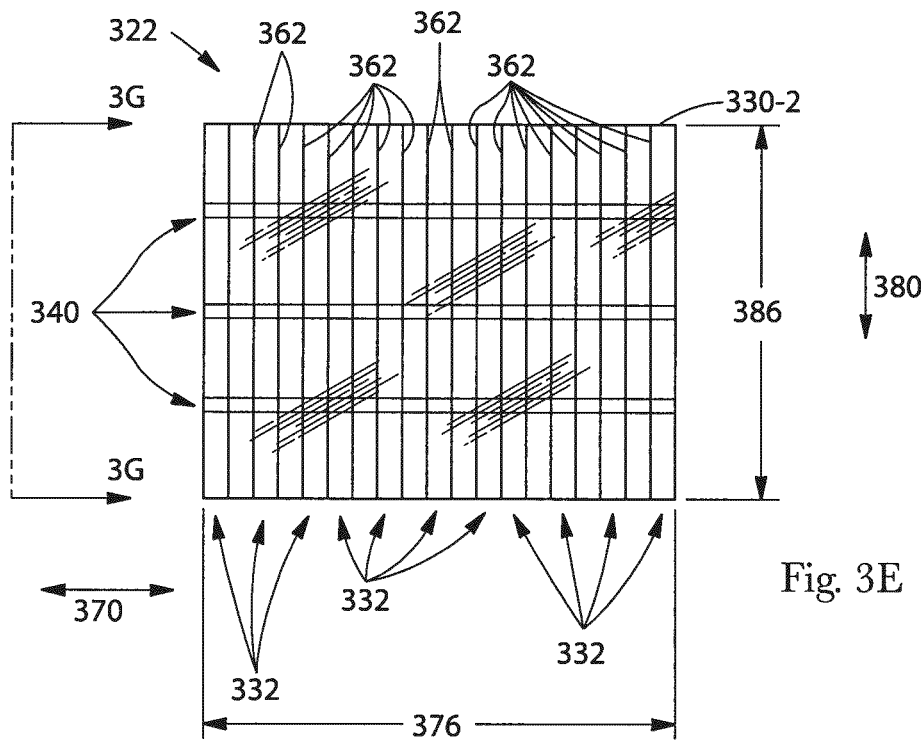
FIG. 3E illustrates a top view of the laminate of FIG. 3B, in a contracted state with micro-texture shown.

FIG. 3E illustrates a top view of the activated laminate 322 of FIG. 3B with micro-texture, in a contracted state. The activated laminate 322 has an overall extended length 376, measured in the primary direction 370, and an overall contracted width 386, measured in the secondary direction 380. The overall contracted width 386 is similar to the overall extended width 384, or slightly less due to contraction of the activated laminate 322. The second layer 330-2 includes a plurality of shirrs 332, which form the micro-texture. The shirrs 332 are the elongated gathers of the material of the second layer 330-2 that are formed when, after the activation process, the first layer 330-1 contracts the laminate 332 in the primary direction 370.

In the embodiment of FIG. 3E, all of the shirrs 332 are parallel with each other and with the secondary direction 380. That is, the shirrs 332 tend to form substantially regular peaks and valleys, wherein the shirrs' 332 direction of elongation extends along in the secondary direction 380. In various embodiments, the shirrs can be oriented within 45 degrees of the secondary direction 380, within 30 degrees of the secondary direction 380, within 15 degrees of the secondary direction 380, or substantially parallel with the secondary direction 380.

In various embodiments, the shirrs 332 can be configured to have various spacings. As examples, the shirrs 332 can be spaced such that there are at least two, at least four, at least eight, at least twelve, at least sixteen, at least twenty, at least twenty five, or at least thirty shirrs per centimeter in the primary direction 370. The spacing of the shirrs 332 may or may not be uniform throughout the activated laminate 322 with micro-texture.

The shirrs 332 have an overall height 392, measured in the tertiary direction 390. As examples, the shirrs 332 can be configured to have an overall height 392 that is less than or about equal to 0.02 millimeters, less than or about equal to 0.04 millimeters, less than or about equal to 0.06 millimeters, less than or about equal to 0.08 millimeters, less than or about equal to 0.1 millimeters, less than or about equal to 0.12 millimeters, less than or about equal to 0.15 millimeters, less than or about equal to 0.2 millimeters, less than or about equal to 0.25 millimeters, less than or about equal to 0.30 millimeters, less than or about equal to 0.40 millimeters, or less than or about equal to 0.50 millimeters.

Figure 3F:
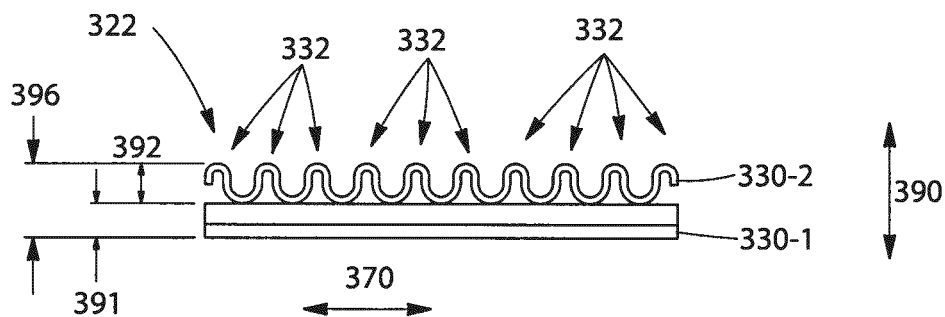
FIG. 3F illustrates a side view of the activated laminate with micro-texture of FIG. 3E.

FIG. 3F illustrates a side view of the activated laminate 322 with micro-texture of FIG. 3E.

Figure 3G:
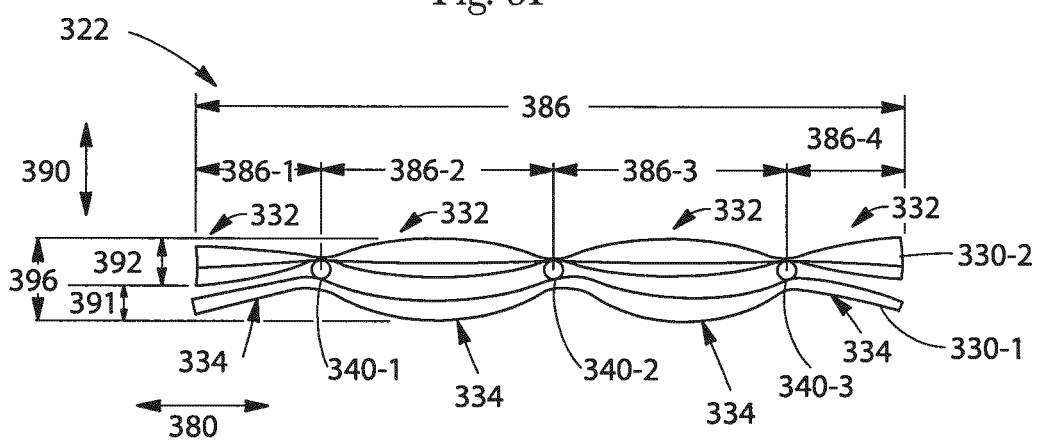
FIG. 3G illustrates an enlarged end view of the activated laminate with micro-texture of FIG. 3E.

FIG. 3G illustrates an enlarged end view of the activated laminate 322 with micro-texture of FIG. 3E. The activated laminate 322 includes a first distance 386-1, a second distance 386-2, a third distance 386-3, and a fourth distance 386-4, which are respectively the same as distances 384-1, 384-2, 384-3, and 384-4, or slightly less due to neckdown and/or plastic deformation from the activation process. The first layer 330-1 includes a plurality of corrugations 334, wherein the first layer 330-1 rises up to each attachment line in the first attachment lines 340 and drops down between the attachment lines. The corrugations 334 are the wave-like ridges and hollows of the material of the first layer 330-1 that are formed when, after the activation process, the overall width of the second layer 330-2 is reduced as the second layer 330-2 forms the shirrs 332.

In the embodiment of FIG. 3G, all of the corrugations 334 are parallel with each other and with the primary direction 370. That is, the corrugations 334 tend to form substantially regular ridges and hollows that extend along in the primary direction 370. In various embodiments, the corrugations can be oriented within 45 degrees of the primary direction 370, within 30 degrees of the primary direction 370, within 15 degrees of the primary direction 370, or substantially parallel with the primary direction 370.

The corrugations 334 have an overall height 391, measured in the tertiary direction 390. As examples, the corrugations 334 can be configured to have an overall height 391 that is less than or about equal to 0.2 millimeters, less than or about equal to 0.4 millimeters, less than or about equal to 0.6 millimeters, less than or about equal to 0.8 millimeters, less than or about equal to 1.0 millimeters, less than or about equal to 1.5 millimeters, less than or about equal to 2.0 millimeters, or less than or about equal to 3.0 millimeters. The corrugations 334 add caliper and softness to the laminate 322.

Figure 4A:
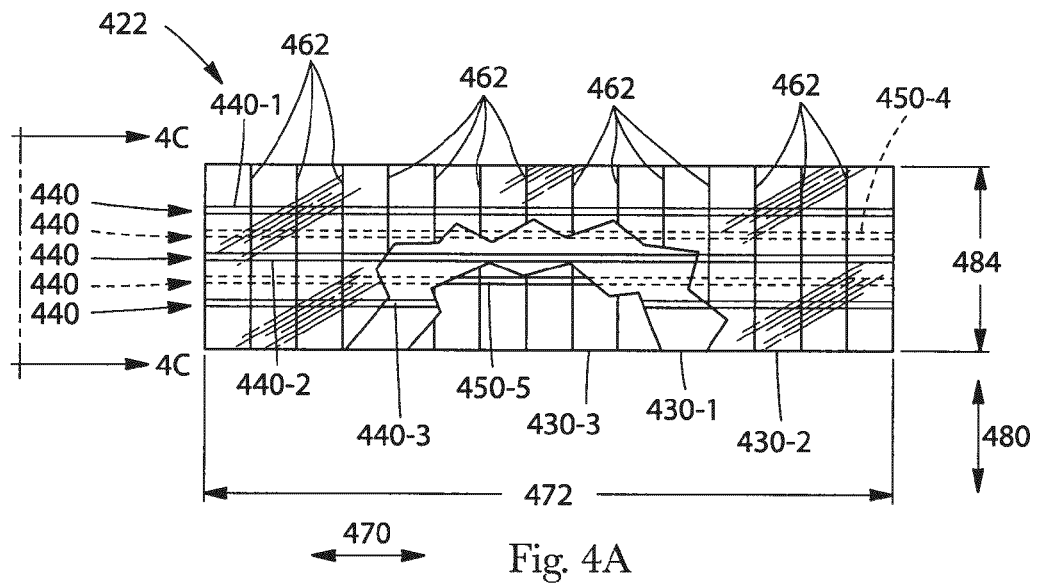
FIG. 4A illustrates a top view of a three-layer laminate of the present disclosure, after activation, in a flat state.

FIG. 4A illustrates a top view of a three-layer laminate 422 of the present disclosure, after activation, in a flat state. The activated laminate 422 is the same as the activated laminate 322, with like numbered elements configured in the same way, except as described below. The intermediate laminate, from which the activated laminate 422 is formed, is not illustrated, although, based on the embodiments of FIGS. 3A-3F, its structure and form will be understood by one of ordinary skill in the art.

In addition to the first layer 430-1 and the second layer 430-2, the activated laminate 422 includes a third layer 430-3. The third layer 430-3 is configured in the same way as the second layer 430-2, with like numbered elements configured in the same way, except as described below. The third layer 430-3 is attached to the first layer 430-1. For purposes of illustration, a portion of the second layer 430-2 and a portion of the first layer 430-1 are shown broken away.

The third layer 430-3 is attached to the first layer 430-1 by a second attachment area that includes second attachment lines 450. The second attachment lines 450 include a fourth line 450-4 and a fifth line 450-5. The second attachment area is configured in the same way as the first attachment area, except that the second attachment lines 450 are positioned differently than the first attachment lines 440. The third layer 430-3 has an overall height 493 that is configured in the same way as the overall height 492 of the second layer 430-2.

Figure 4B:
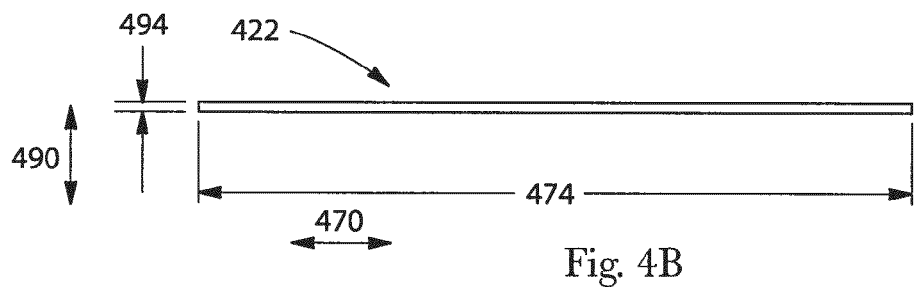
FIG. 4B illustrates a side view of the activated laminate of FIG. 4A.

FIG. 4B illustrates a side view of the activated laminate 422 of FIG. 4A.

Figure 4C:
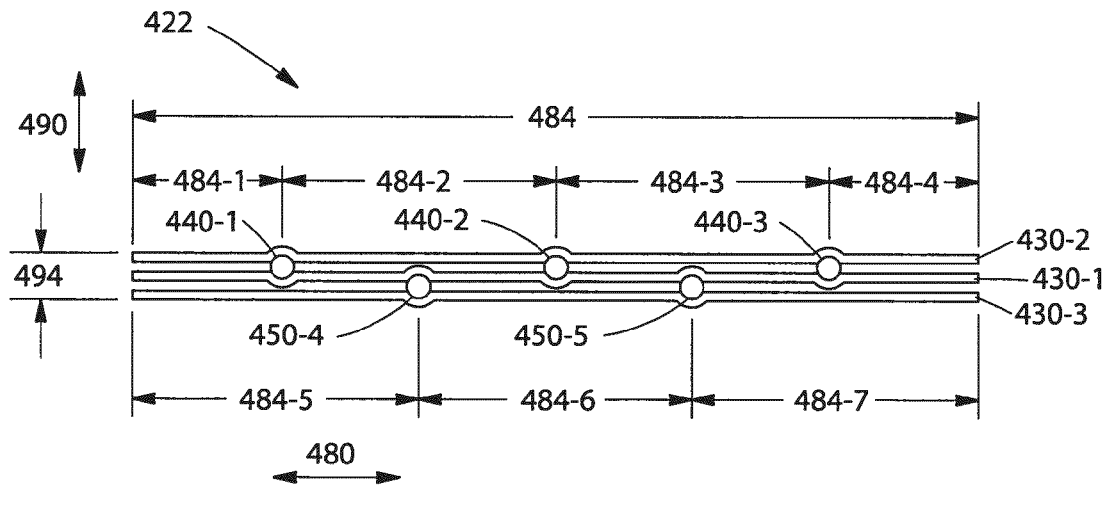
FIG. 4C illustrates an end view of the activated laminate of FIG. 4A.

FIG. 4C illustrates an end view of the activated laminate of FIG. 4A. The fourth line 450-4 is spaced apart from the left edge of the activated laminate 422 by a fifth distance 484-5, measured in the secondary direction 480 from the left edge to the center of the fourth line 450-4. The fifth line 450-5 is spaced apart from the fourth line 450-4 by a sixth distance 484-6, measured in the secondary direction 480 from the center of the fourth line 450-4 to the center of the fifth line 450-5. The fifth line 450-5 is also spaced apart from the right edge of the activated laminate 422 by a seventh distance 484-7, measured in the secondary direction 480 from the center of the fifth line 450-5 to the right edge. In the embodiment of FIG. 4C, the fourth line 450-4 is positioned intermediate the first line 440-1 and the second line 440-2, while the fifth line 450-5 is positioned intermediate the second line 440-2 and the third line 440-3. In some embodiments, the second attachment lines 450 can be positioned halfway between the first attachment lines 440.

In various embodiments, the second attachment lines 450 can have substantially uniform or uniform spacing. The second attachment lines 450 can be spaced apart from each other by the same distances as the first attachment lines 440 are spaced apart or by different distances.

Figure 4D:
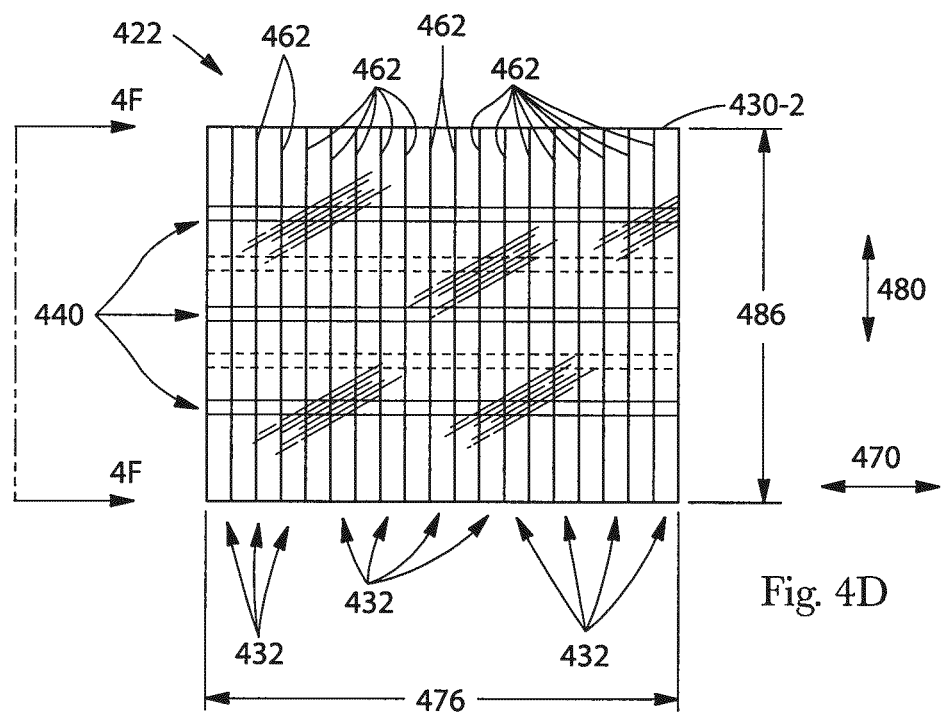
FIG. 4D illustrates a top view of the laminate of FIG. 4A, in a contracted state with micro-texture shown.

FIG. 4D illustrates a top view of the laminate 422 of FIG. 4A with micro-texture, in a contracted state.

Figure 4E:
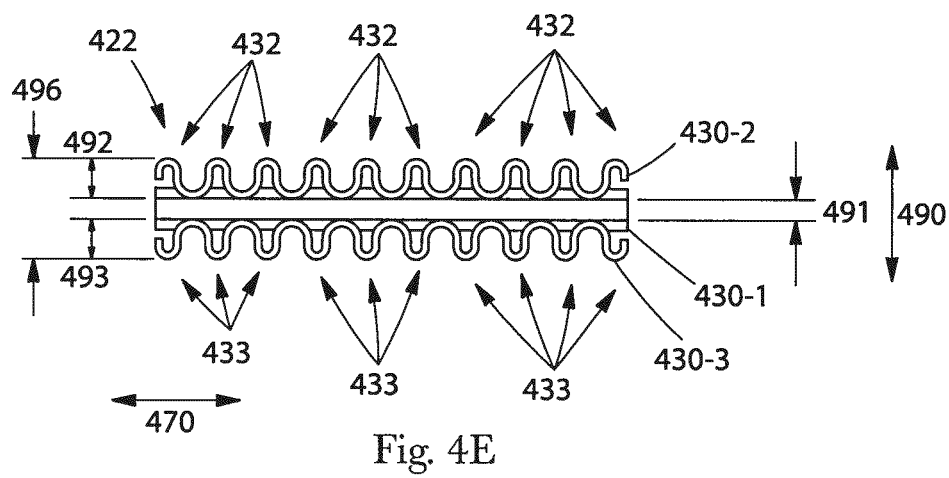
FIG. 4E illustrates a side view of the activated laminate with micro-texture of FIG. 4D.

FIG. 4E illustrates a side view of the activated laminate 422 of FIG. 4A with micro-texture. The third layer 430-3 includes shirrs 433, which are configured in the same way as the shirrs 432 of the second layer 430-2.

Figure 4F:
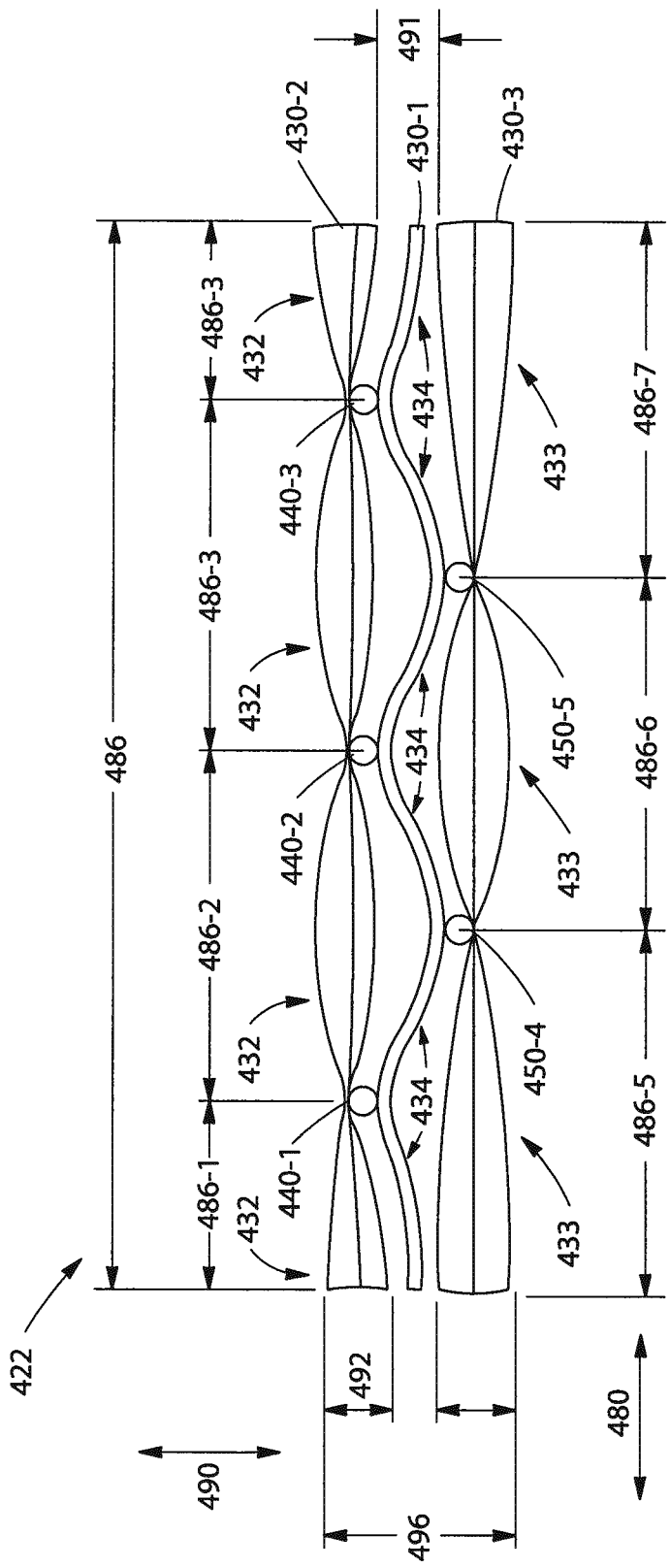
FIG. 4F illustrates an enlarged end view of the activated laminate with micro-texture of FIG. 4D.

FIG. 4F illustrates an enlarged end view of the activated laminate of FIG. 4A with micro-texture. The activated laminate 422 includes a first distance 486-1, a second distance 486-2, a third distance 486-3, a fourth distance 486-4, a fifth distance 486-5, a sixth distance 486-6, and a seventh distance 486-7, which are respectively the same as distances 484-1, 484-2, 484-3, 484-4, 484-5, 484-6, and 484-7, or slightly less due to contraction of the activated laminate 422. The first layer 430-1 includes a plurality of corrugations 434, wherein the first layer 430-1 rises up to each attachment line in the first attachment lines 440 and drops down to each attachment line in the second attachment lines 450.

Figure 5A:
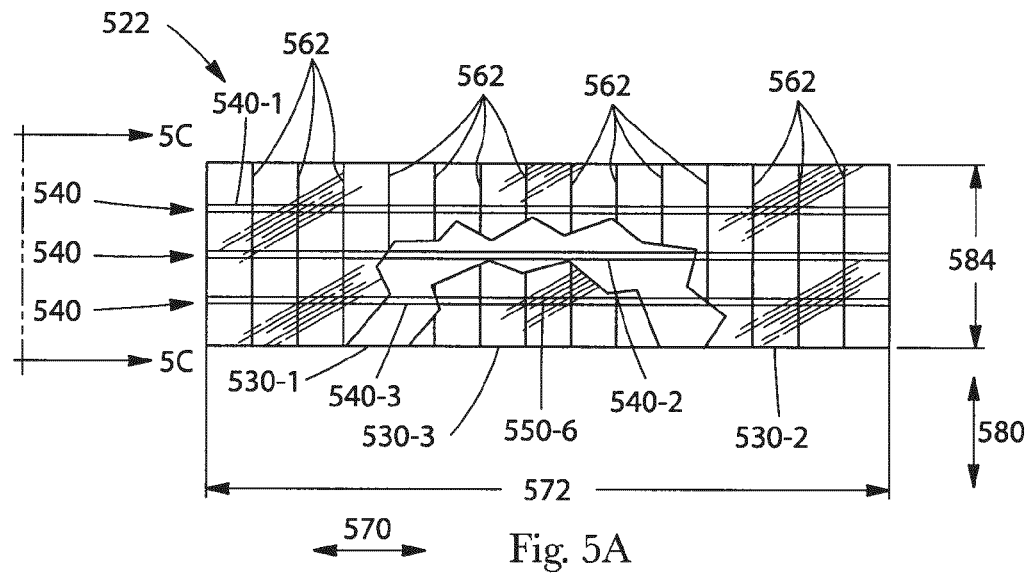
FIG. 5A illustrates a top view of an alternate embodiment of a three-layer laminate of the present disclosure, after activation, in a flat state.

FIG. 5A illustrates a top view of an alternate embodiment of a three-layer laminate 522 of the present disclosure, after activation, in a flat state. The activated laminate 522 is the same as the activated laminate 422, with like numbered elements configured in the same way, except as described below. The second attachment lines 550 include a fourth line 550-4, a fifth line 550-5, and a sixth line 550-6, which are positioned the same as the first attachment lines 540.

Figure 5B:
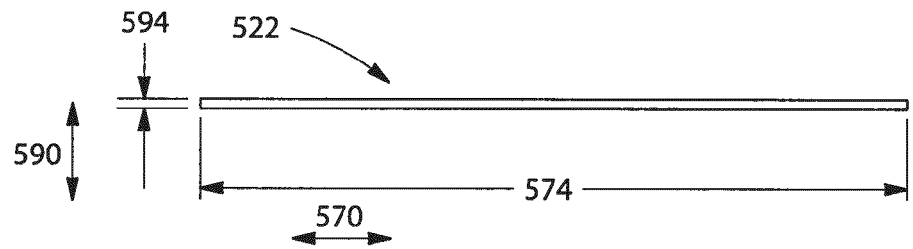
FIG. 5B illustrates a side view of the activated laminate of FIG. 5A.

FIG. 5B illustrates a side view of the activated laminate 522 of FIG. 5A.

Figure 5C:
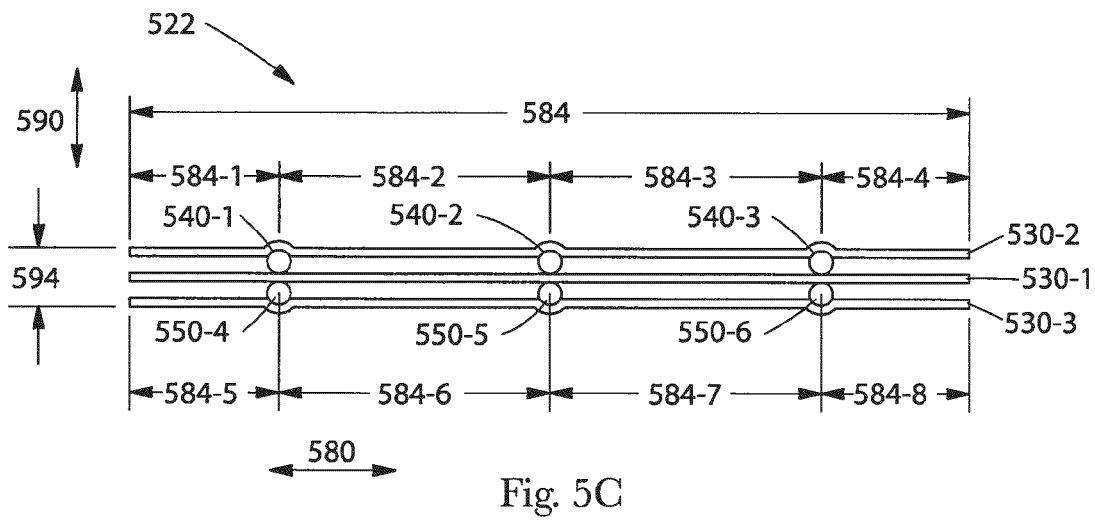
FIG. 5C illustrates an end view of the activated laminate of FIG. 5A.

FIG. 5C illustrates an end view of the activated laminate of FIG. 5A. The fourth line 550-4 is aligned subjacent the first line 540-1, the fifth line 550-5 is aligned subjacent the second line 540-2, and the sixth line 550-6 is aligned subjacent the third line 540-3. The second attachment lines 550 are spaced with distances 584-5, 584-6, 584-7, and 584-8, which are the same as the distances 584-1, 584-2, 584-3, and 584-4 for the first attachment lines 540, respectively.

The intermediate laminate, from which the activated laminate 522 is formed, and the activated laminate 522 in a contracted state are not illustrated, although, based on the other embodiments of the present disclosure, their structure and form will be understood by one of ordinary skill in the art.

Figure 6A:
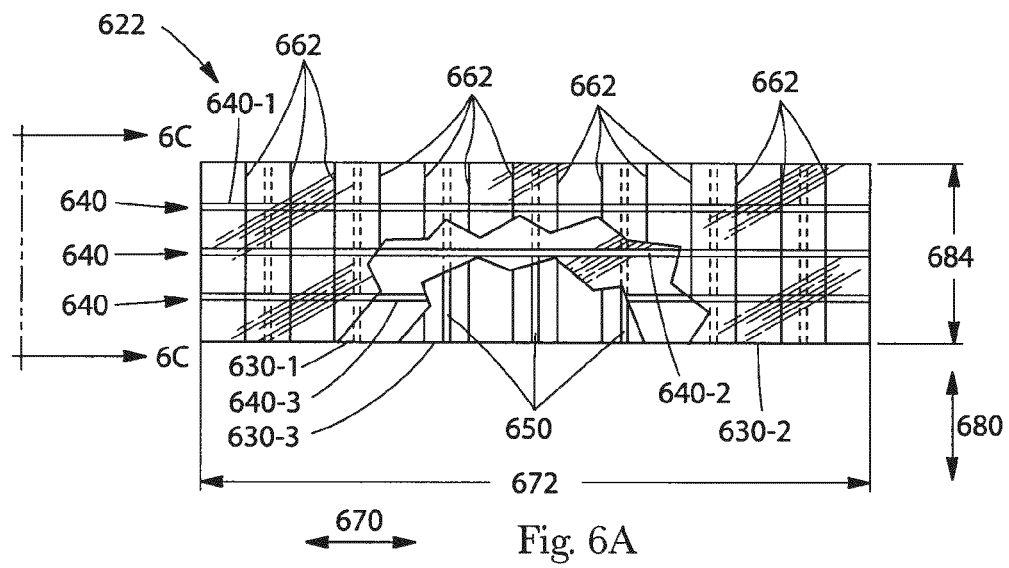
FIG. 6A illustrates a top view of another alternate embodiment of a three-layer laminate of the present disclosure, after activation, in a flat state.

FIG. 6A illustrates a top view of another alternate embodiment of a three-layer laminate 622 of the present disclosure, after activation, in a flat state. The activated laminate 622 is the same as the activated laminate 522, with like numbered elements configured in the same way, except as described below. The second attachment lines 650 are positioned differently than the second attachment lines 640.

Figure 6B:
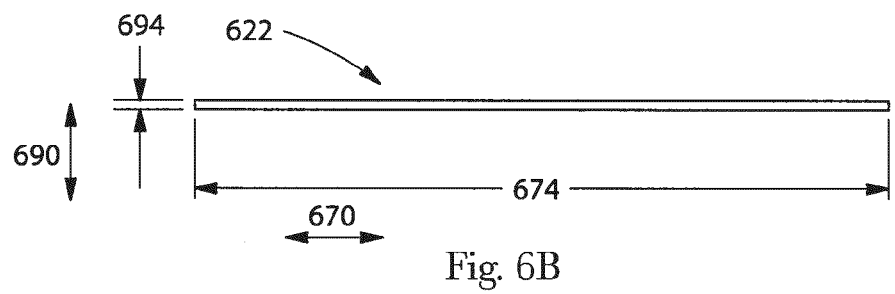
FIG. 6B illustrates a side view of the activated laminate of FIG. 6A.

FIG. 6B illustrates a side view of the activated laminate 622 of FIG. 6A.

Figure 6C:
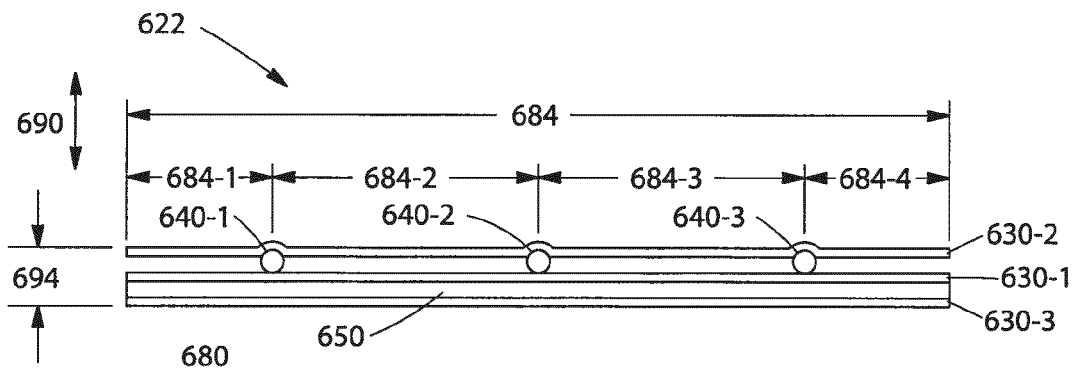
FIG. 6C illustrates an end view of the activated laminate of FIG. 6A.

FIG. 6C illustrates an end view of the activated laminate 622 of FIG. 6A. The second attachment lines 650 are oriented orthogonal to the second attachment lines 550. Instead of being oriented in the primary direction 670, the second attachment lines 650 are oriented in the secondary direction 680.

The intermediate laminate, from which the activated laminate 622 is formed, and the activated laminate 622 in a contracted state are not illustrated, although, based on the other embodiments of the present disclosure, their structure and form will be understood by one of ordinary skill in the art.

Figure 7A:
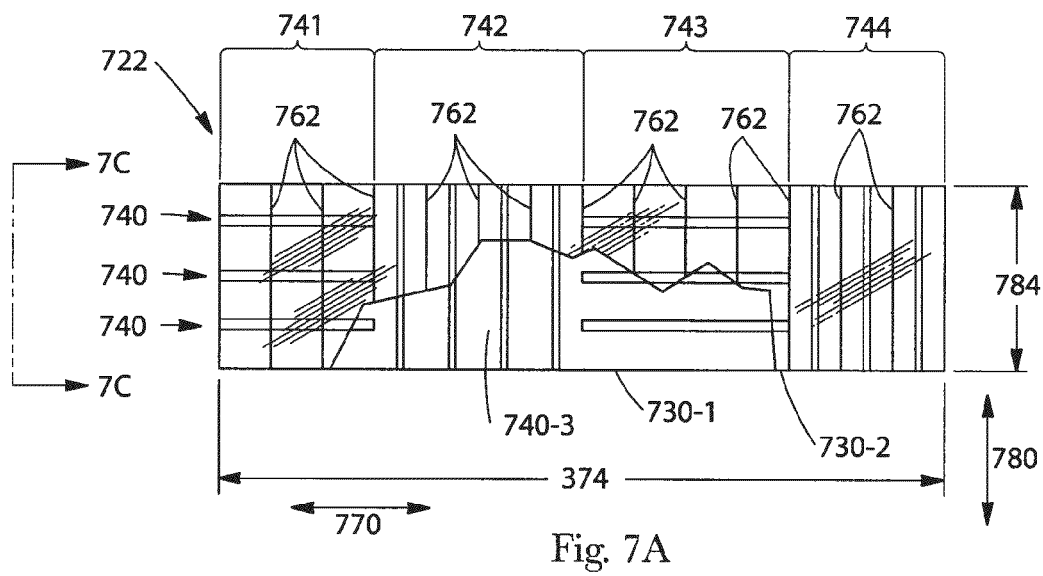
FIG. 7A illustrates a top view of an alternate embodiment of a two-layer laminate of the present disclosure, after activation, in a flat state.

FIG. 7A illustrates a top view of an alternate embodiment of a two-layer laminate 722 of the present disclosure, after activation, in a flat state. The activated laminate 722 is the same as the activated laminate 322, with like numbered elements configured in the same way, except as described below. The first attachment lines 740 are positioned differently than the first attachment lines 340. Instead of being continuous straight lines, the first attachment lines 740 are groups of parallel line segments. A first group 741 includes line segments oriented in a direction parallel with the primary direction 770. A second group 742 includes line segments oriented in a direction parallel with the secondary direction 780. A third group 743 includes line segments oriented in a direction parallel with the primary direction 770. A fourth group 744 includes line segments oriented in a direction parallel with the secondary direction 780. In various embodiments, this repeating pattern can be shortened or lengthened, with an increased or decreased number of such groups.

Figure 7B:
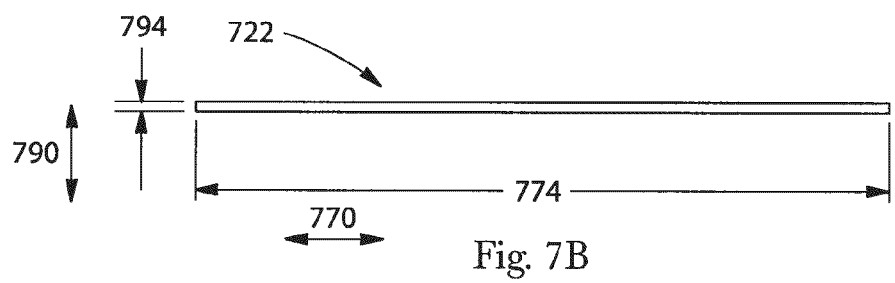
FIG. 7B illustrates a side view of the activated laminate of FIG. 7A.

FIG. 7B illustrates a side view of the activated laminate 722 of FIG. 7A.

Figure 7C:
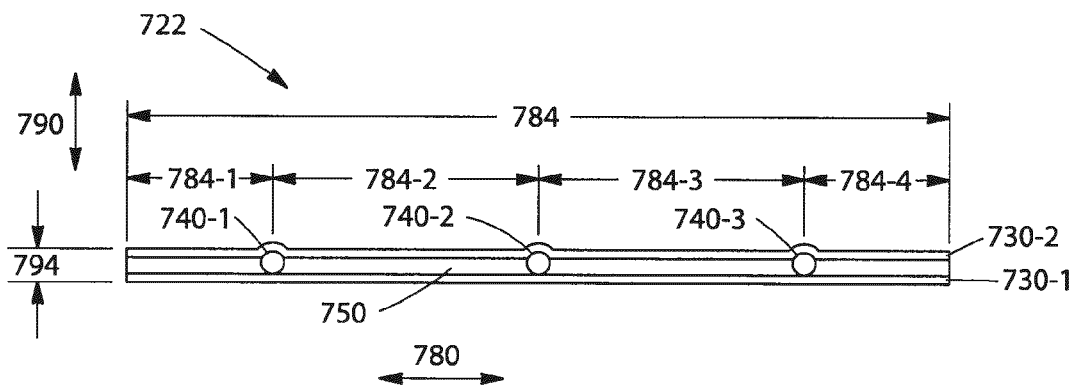
FIG. 7C illustrates an end view of the activated laminate of FIG. 7A.

FIG. 7C illustrates an end view of the activated laminate 722 of FIG. 7A.

The intermediate laminate, from which the activated laminate 722 is formed, and the activated laminate 722 in a contracted state are not illustrated, although, based on the other embodiments of the present disclosure, their structure and form will be understood by one of ordinary skill in the art.

FIGS. 8A-15B illustrate exemplary embodiments of attachment lines that can be used as first attachment lines and/or as second attachment lines with any embodiment of the present disclosure. Throughout FIGS. 8A-15B, elements correspond with like numbered elements in other figures, unless otherwise stated. It is contemplated that any of the embodiments of attachment lines in FIGS. 8A-15B can alternatively be configured in an orthogonal orientation with respect to a laminate (i.e. in the secondary direction, instead of the primary direction), or at any angle, with respect to the primary direction and the secondary direction of a laminate.

Figure 8A:
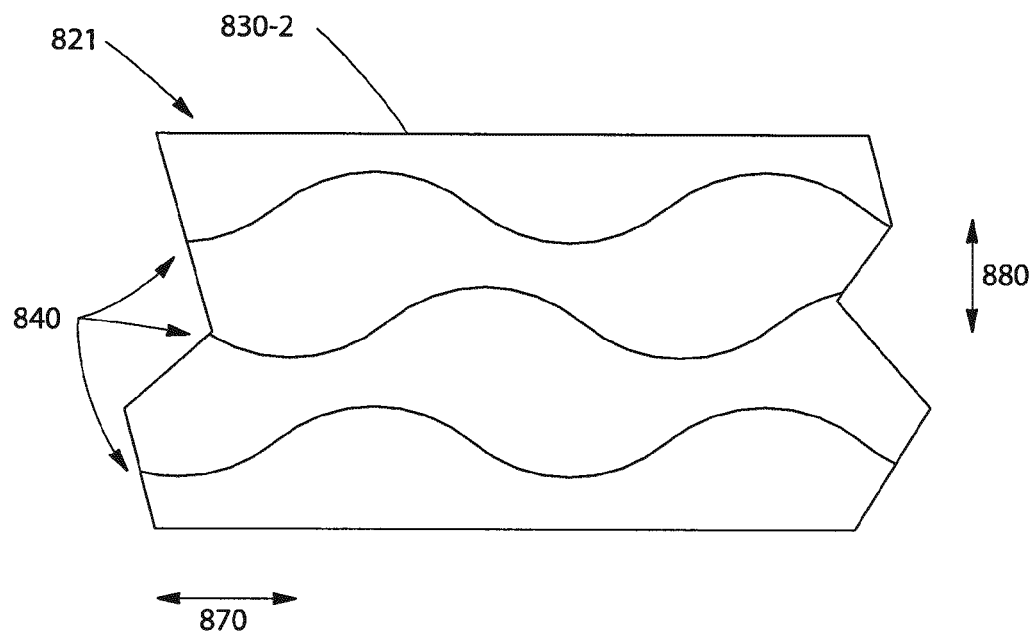
FIG. 8A illustrates a top view of a laminate of the present disclosure, with curved attachment lines, before activation.

FIG. 8A illustrates a top view of an intermediate laminate 821 of the present disclosure, with curved first attachment lines 840, before activation. The intermediate laminate 821 includes a second layer 830-2, a primary direction 870, and a secondary direction 880.

Figure 8B:
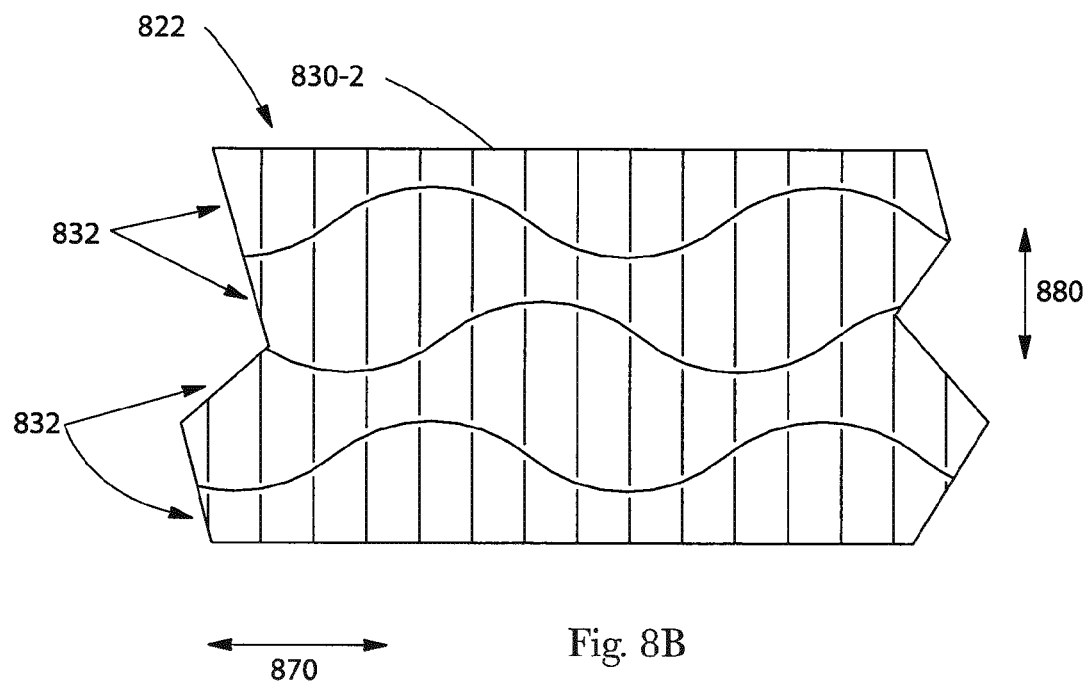
FIG. 8B illustrates a top view of the laminate of FIG. 8A, after activation, with micro-texture.

FIG. 8B illustrates a top view of an activated laminate 822 with micro-texture, which is the intermediate laminate 821 of FIG. 8A, after activation. The activated laminate 822 includes a plurality of shirrs 832 in the second layer 830-2, wherein the shirrs 832 are oriented in the secondary direction 880.

Figure 9A:
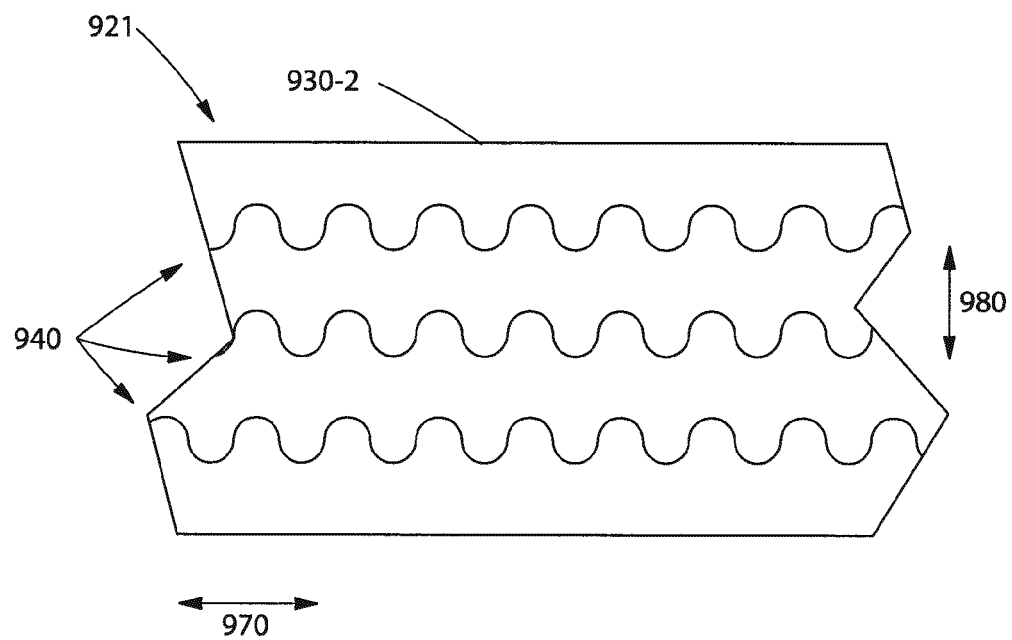
FIG. 9A illustrates a top view of a laminate of the present disclosure, with oscillating attachment lines, before activation.

FIG. 9A illustrates a top view of an intermediate laminate 921 of the present disclosure, with oscillating first attachment lines 940, before activation. In various embodiments, the oscillating first attachment lines 940 can be provided in the Omega™ pattern by the ITW of Glenview, Ill. The intermediate laminate 921 includes a second layer 930-2, a primary direction 970, and a secondary direction 980.

Figure 9B:
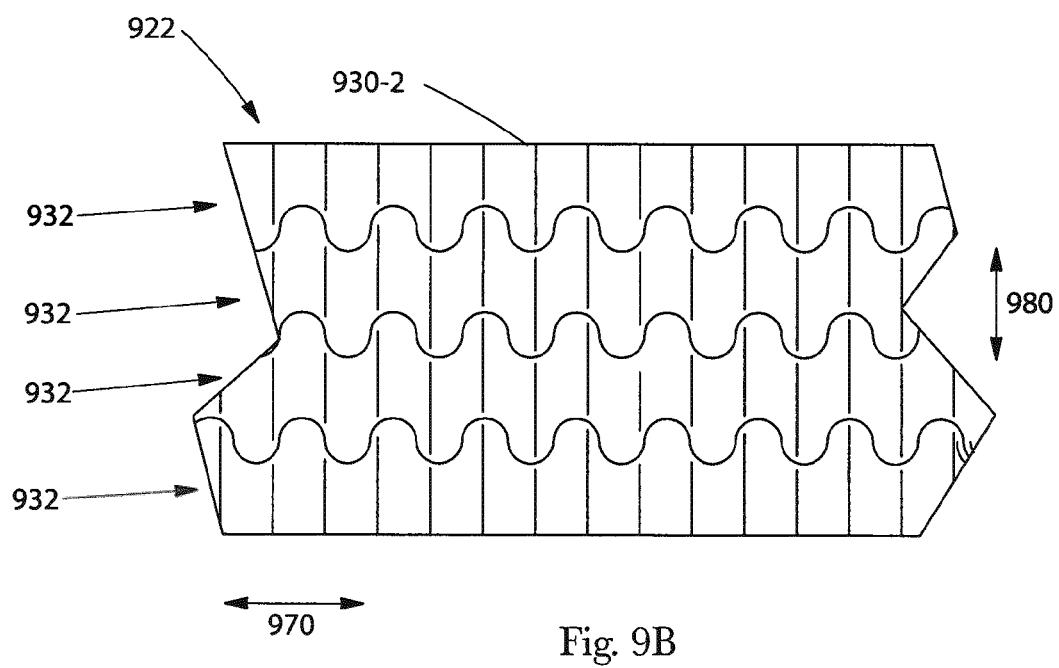
FIG. 9B illustrates a top view of the laminate of FIG. 9A, after activation, with micro-texture.

FIG. 9B illustrates a top view of an activated laminate 922 with micro-texture, which is the intermediate laminate 921 of FIG. 9A, after activation. The activated laminate 922 includes a plurality of shirrs 932 in the second layer 930-2, wherein the shirrs 932 are oriented in the secondary direction 980.

Figure 10A:
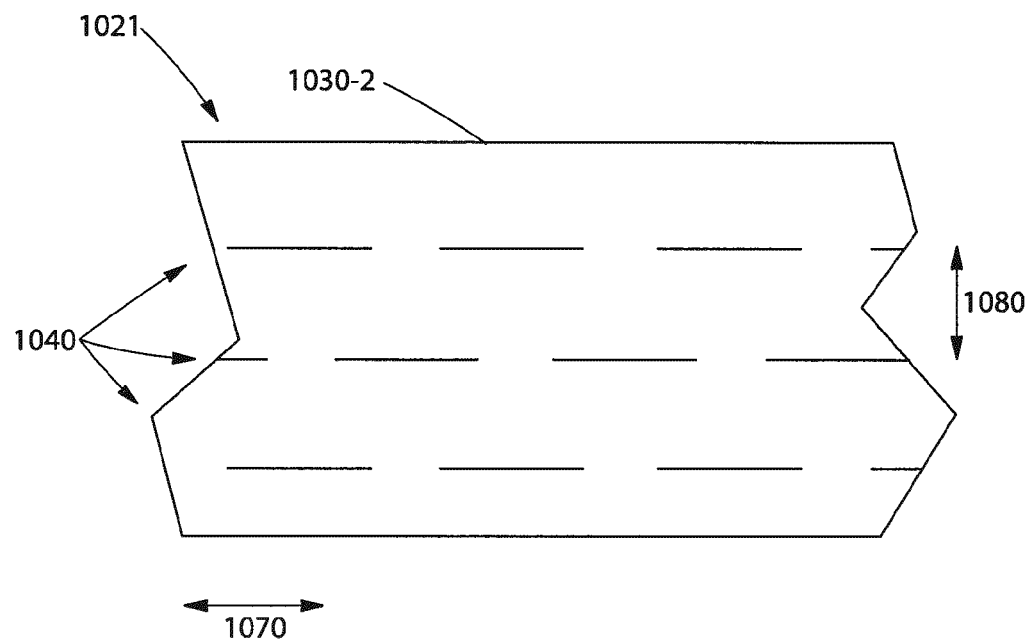
FIG. 10A illustrates a top view of a laminate of the present disclosure, with attachment lines comprising a series of dashes, before activation.

FIG. 10A illustrates a top view of an intermediate laminate 1021 of the present disclosure, with first attachment lines 1040 comprising a series of dashes, before activation. The intermediate laminate 1021 includes a second layer 1030-2, a primary direction 1070, and a secondary direction 1080.

Figure 10B:
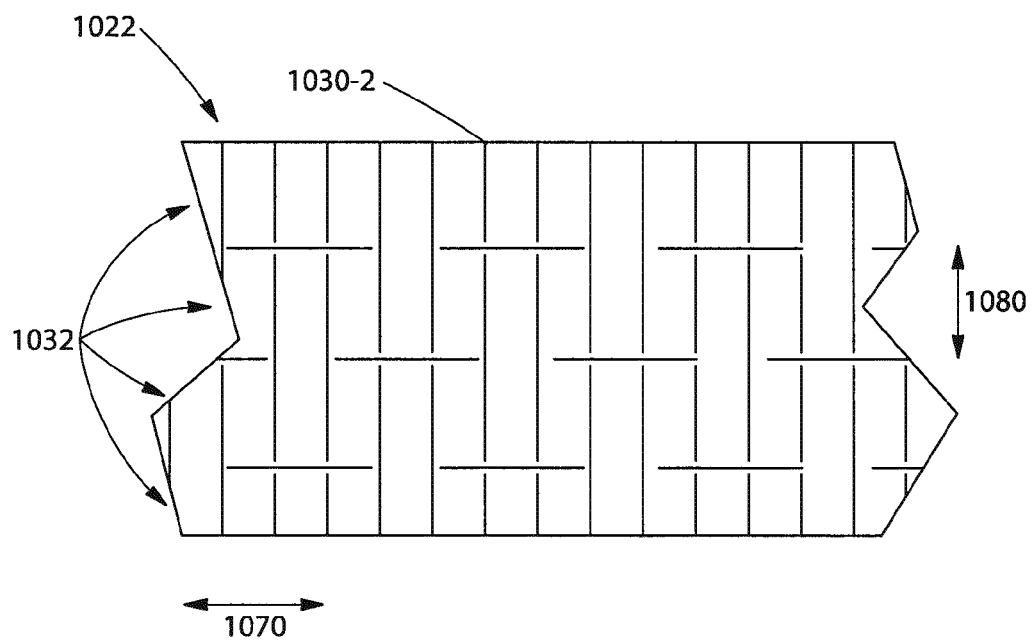
FIG. 10B illustrates a top view of the laminate of FIG. 10A, after activation, with micro-texture.

FIG. 10B illustrates a top view of an activated laminate 1022 with micro-texture, which is the intermediate laminate 1021 of FIG. 10A, after activation. The activated laminate 1022 includes a plurality of shirrs 1032 in the second layer 1030-2, wherein the shirrs 1032 are oriented in the secondary direction 1080.

Figure 11A:
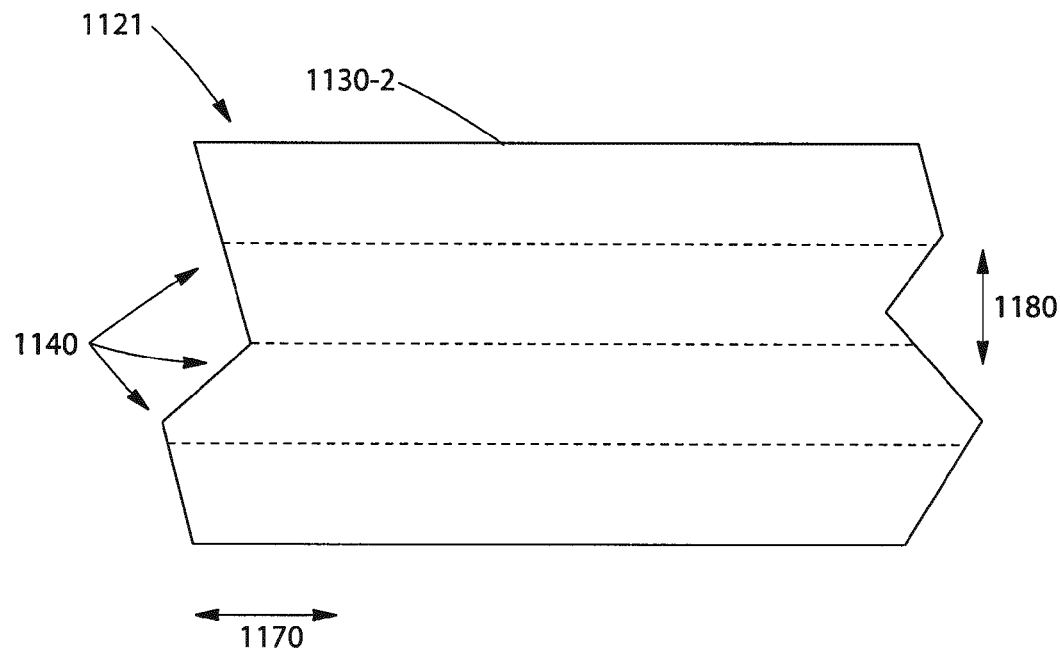
FIG. 11A illustrates a top view of a laminate of the present disclosure, with attachment lines comprising a series of dots, before activation.

FIG. 11A illustrates a top view of an intermediate laminate 1121 of the present disclosure, with first attachment lines 1140 comprising a series of dots, before activation. The intermediate laminate 1121 includes a second layer 1130-2, a primary direction 1170, and a secondary direction 1180.

Figure 11B:
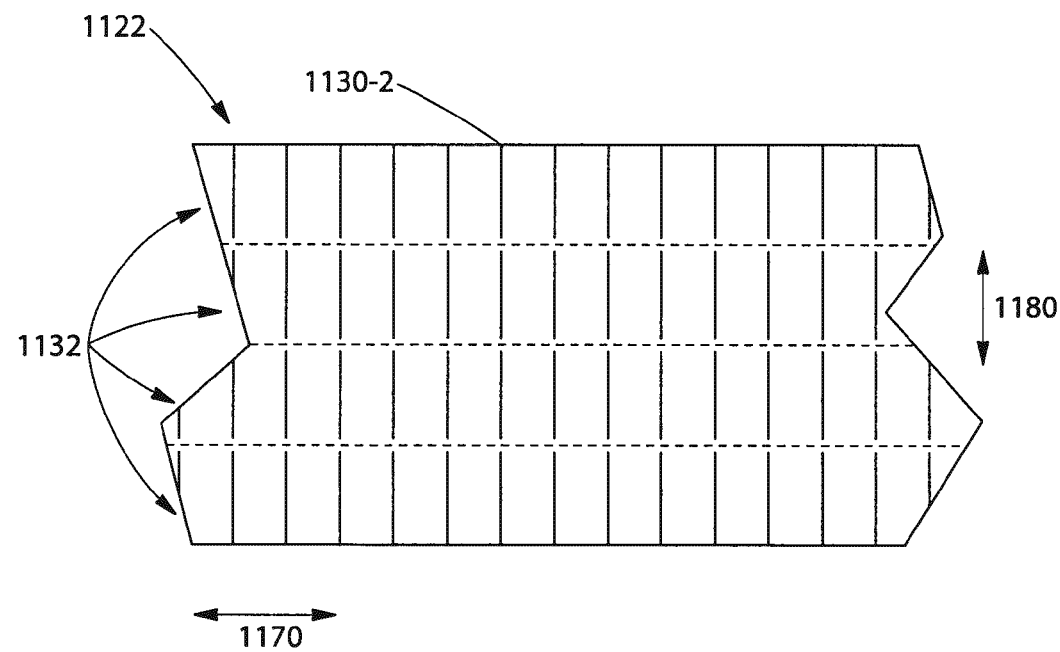
FIG. 11B illustrates a top view of the laminate of FIG. 11A, after activation, with micro-texture.

FIG. 11B illustrates a top view of an activated laminate 1122 with micro-texture, which is the intermediate laminate 1121 of FIG. 11A, after activation. The activated laminate 1122 includes a plurality of shirrs 1132 in the second layer 1130-2, wherein the shirrs 1132 are oriented in the secondary direction 1180.

Figure 12A:
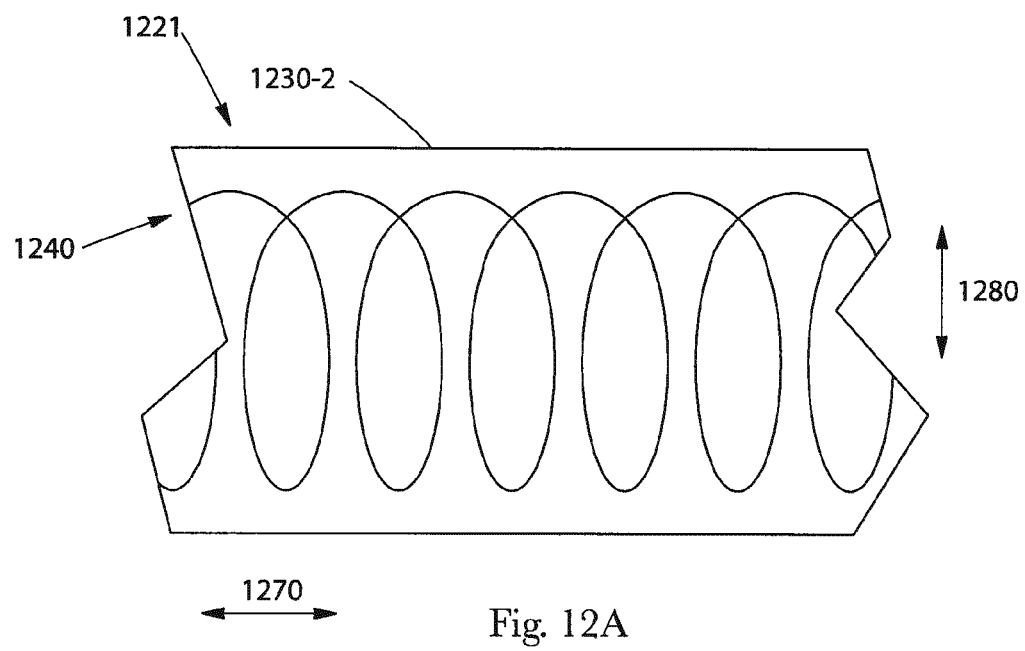
FIG. 12A illustrates a top view of a laminate of the present disclosure, with attachment lines having a single open spiral pattern, before activation.

FIG. 12A illustrates a top view of an intermediate laminate 1221 of the present disclosure, with first attachment lines 1240 having a single open spiral pattern, before activation. The intermediate laminate 1221 includes a second layer 1230-2, a primary direction 1270, and a secondary direction 1280.

Figure 12B:
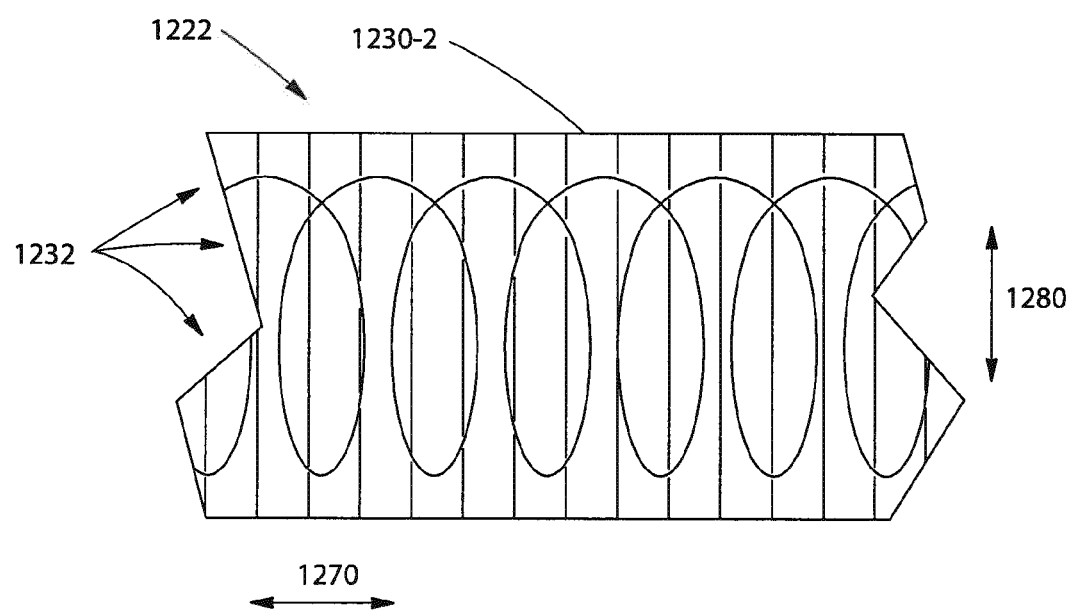
FIG. 12B illustrates a top view of the laminate of FIG. 12A, after activation, with micro-texture.

FIG. 12B illustrates a top view of an activated laminate 1222 with micro-texture, which is the intermediate laminate 1221 of FIG. 12A, after activation. The activated laminate 1222 includes a plurality of shirrs 1232 in the second layer 1230-2, wherein the shirrs 1232 are oriented in the secondary direction 1280.

Figure 13A:
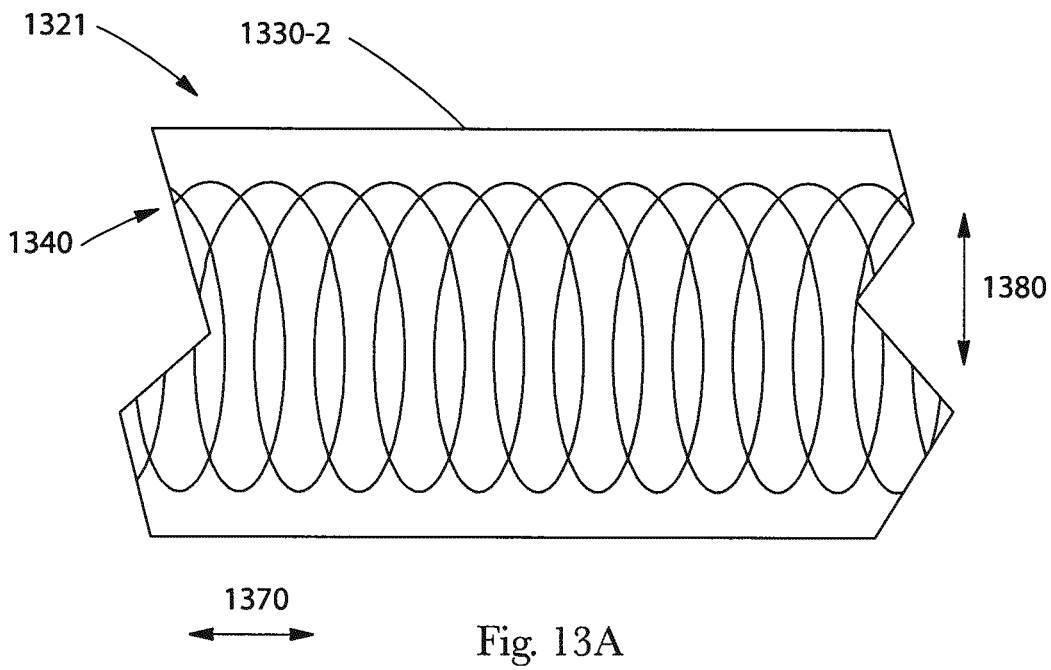
FIG. 13A illustrates a top view of a laminate of the present disclosure, with attachment lines having a single tight spiral pattern, before activation.

FIG. 13A illustrates a top view of an intermediate laminate 1321 of the present disclosure, with first attachment lines 1340 having a single tight spiral pattern, before activation. The intermediate laminate 1321 includes a second layer 1330-2, a primary direction 1370, and a secondary direction 1380.

Figure 13B:
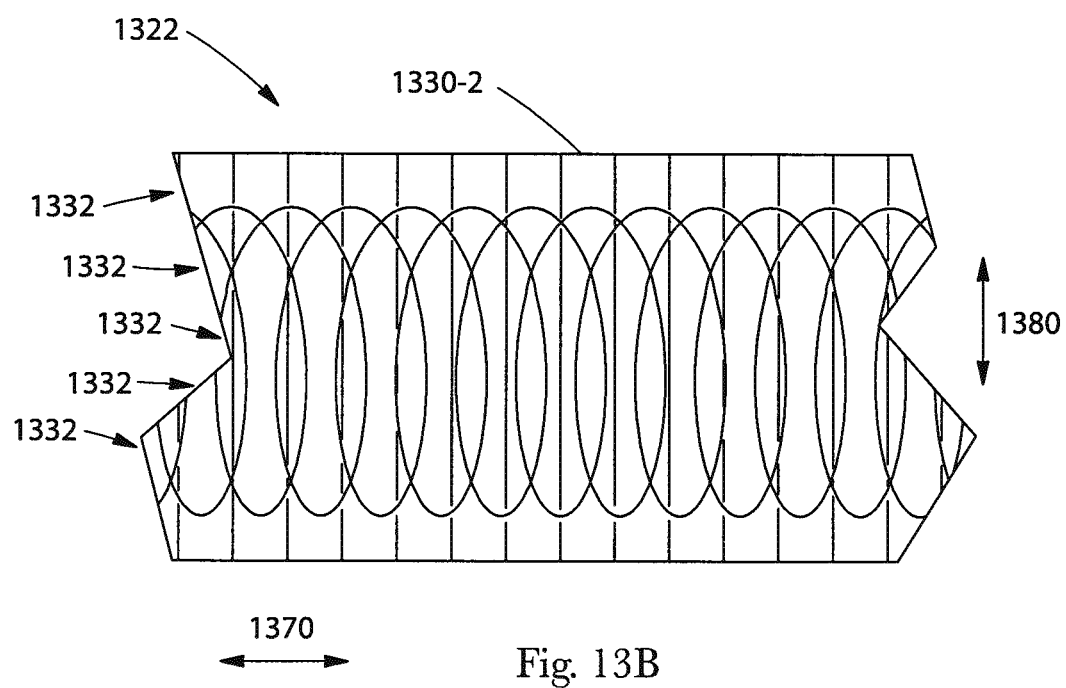
FIG. 13B illustrates a top view of the laminate of FIG. 13A, after activation, with micro-texture.

FIG. 13B illustrates a top view of an activated laminate 1322 with micro-texture, which is the intermediate laminate 1321 of FIG. 13A, after activation. The activated laminate 1322 includes a plurality of shirrs 1332 in the second layer 1330-2, wherein the shirrs 1332 are oriented in the secondary direction 1380.

Figure 14A:
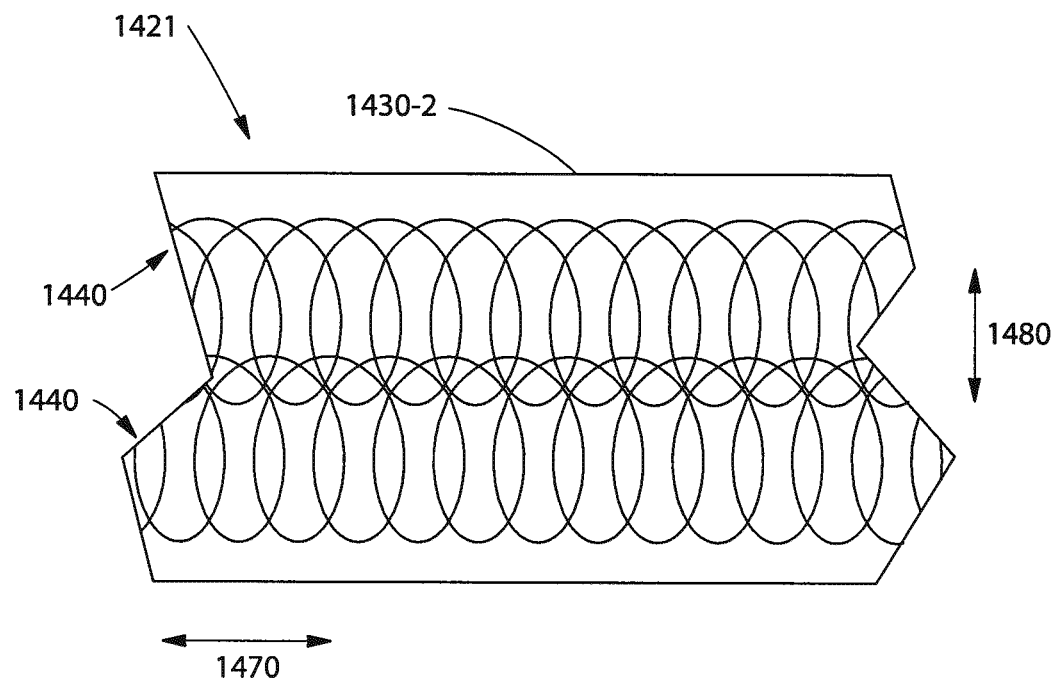
FIG. 14A illustrates a top view of a laminate of the present disclosure, with attachment lines having a dual tight spiral pattern, before activation.

FIG. 14A illustrates a top view of an intermediate laminate 1421 of the present disclosure, with first attachment lines 1440 having a dual tight spiral pattern, before activation. The intermediate laminate 1421 includes a second layer 1430-2, a primary direction 1470, and a secondary direction 1480.

Figure 14B:
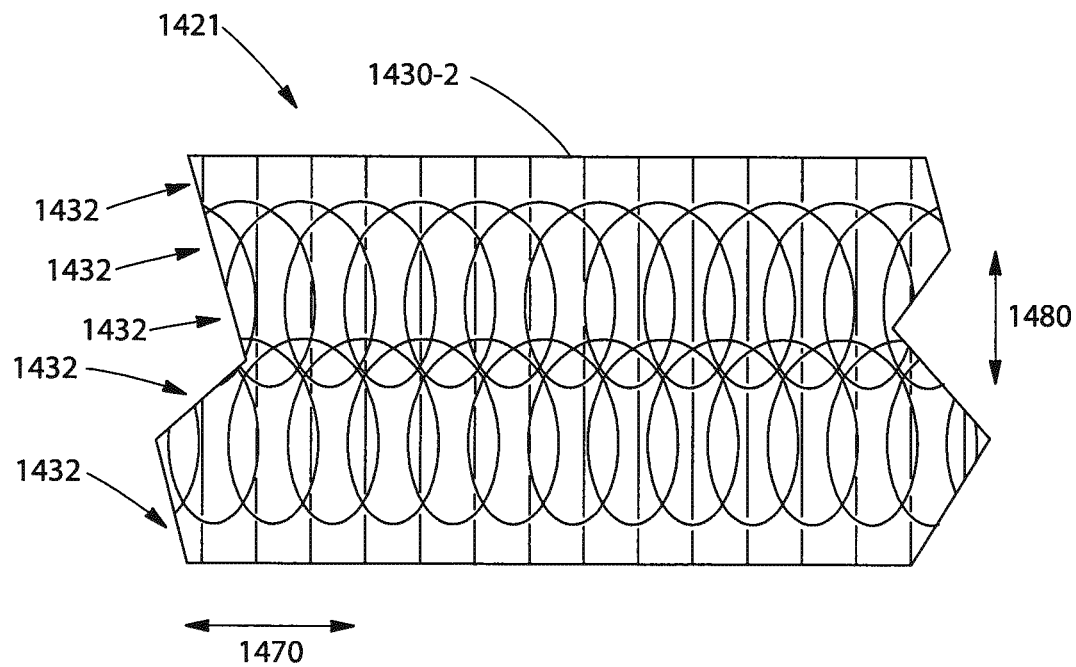
FIG. 14B illustrates a top view of the laminate of FIG. 14A, after activation, with micro-texture.

FIG. 14B illustrates a top view of an activated laminate 1422 with micro-texture, which is the intermediate laminate 1421 of FIG. 14A, after activation. The activated laminate 1422 includes a plurality of shirrs 1432 in the second layer 1430-2, wherein the shirrs 1432 are oriented in the secondary direction 1480.

Figure 15A:
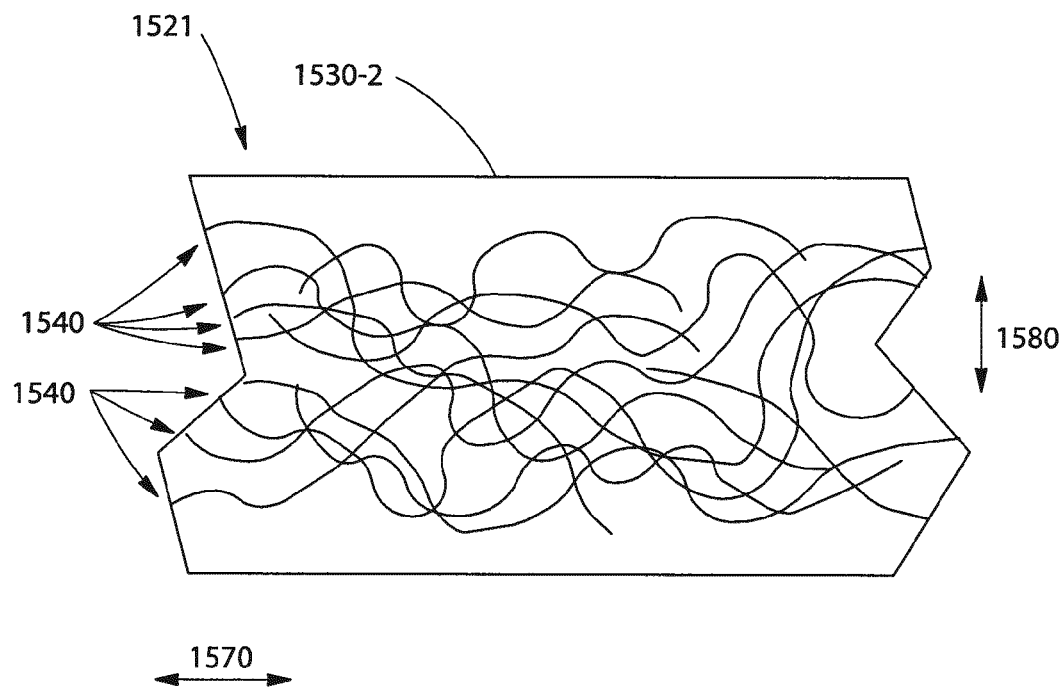
FIG. 15A illustrates a top view of a laminate of the present disclosure, with randomly oriented attachment lines, before activation.

FIG. 15A illustrates a top view of an intermediate laminate 1521 of the present disclosure, with randomly oriented first attachment lines 1540 having a dual tight spiral pattern, before activation. The intermediate laminate 1521 includes a second layer 1530-2, a primary direction 1570, and a secondary direction 1580.

Figure 15B:
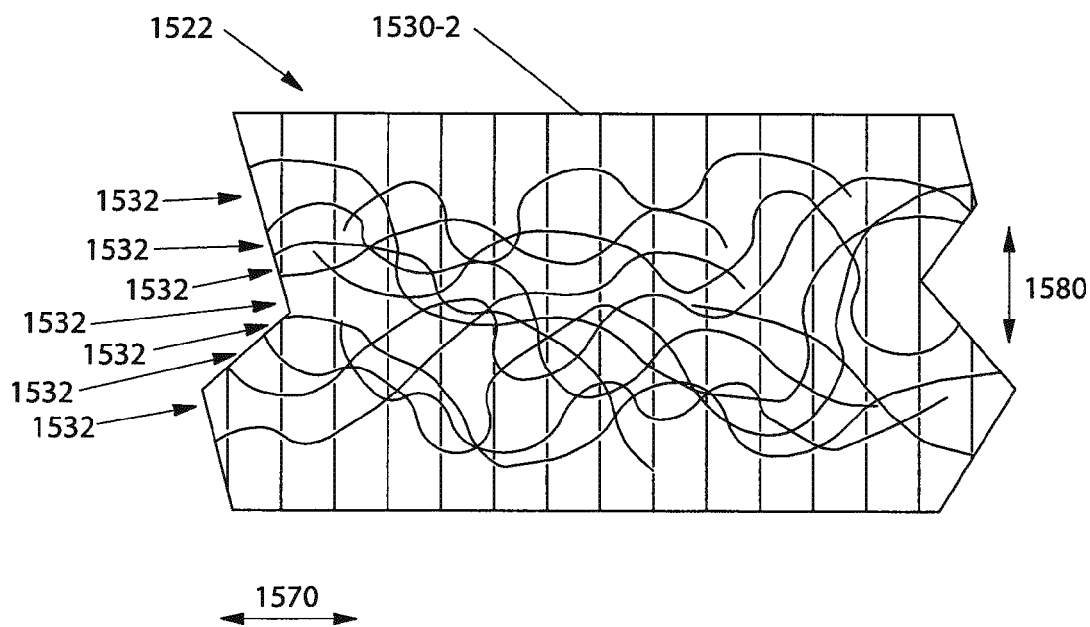
FIG. 15B illustrates a top view of the laminate of FIG. 15A, after activation, with micro-texture.

FIG. 15B illustrates a top view of an activated laminate 1522 with micro-texture, which is the intermediate laminate 1521 of FIG. 15A, after activation. The activated laminate 1522 includes a plurality of shirrs 1532 in the second layer 1530-2, wherein the shirrs 1532 are oriented in the secondary direction 1580.

Figure 16A:
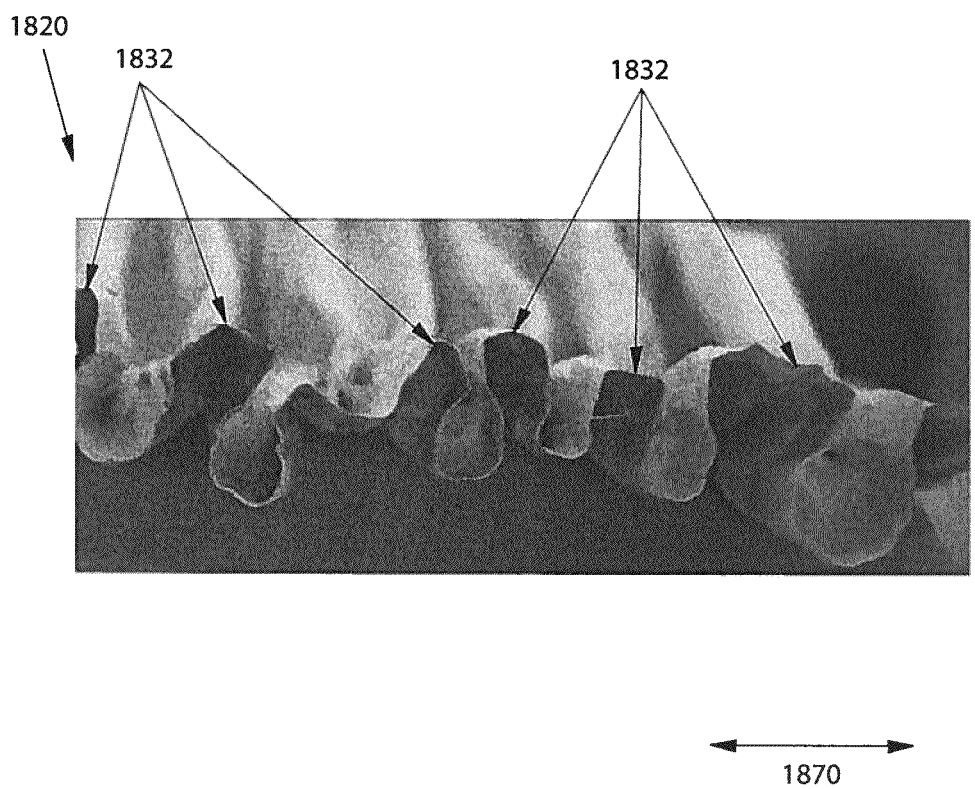
FIG. 16A is a microscopic photograph of an outer edge of an activated laminate with micro-texture of the present disclosure, in a contracted state.

FIG. 16A is a microscopic photograph of an outer edge of an activated laminate 1820 with micro-texture of the present disclosure. FIG. 16A shows some close-up detail of shirrs 1832 on the laminate 1820. In FIG. 16A, there are about five shirrs over a distance of about 1.8 millimeters in a primary direction 1870, or about 28 shirrs per centimeter.

Figure 16B:
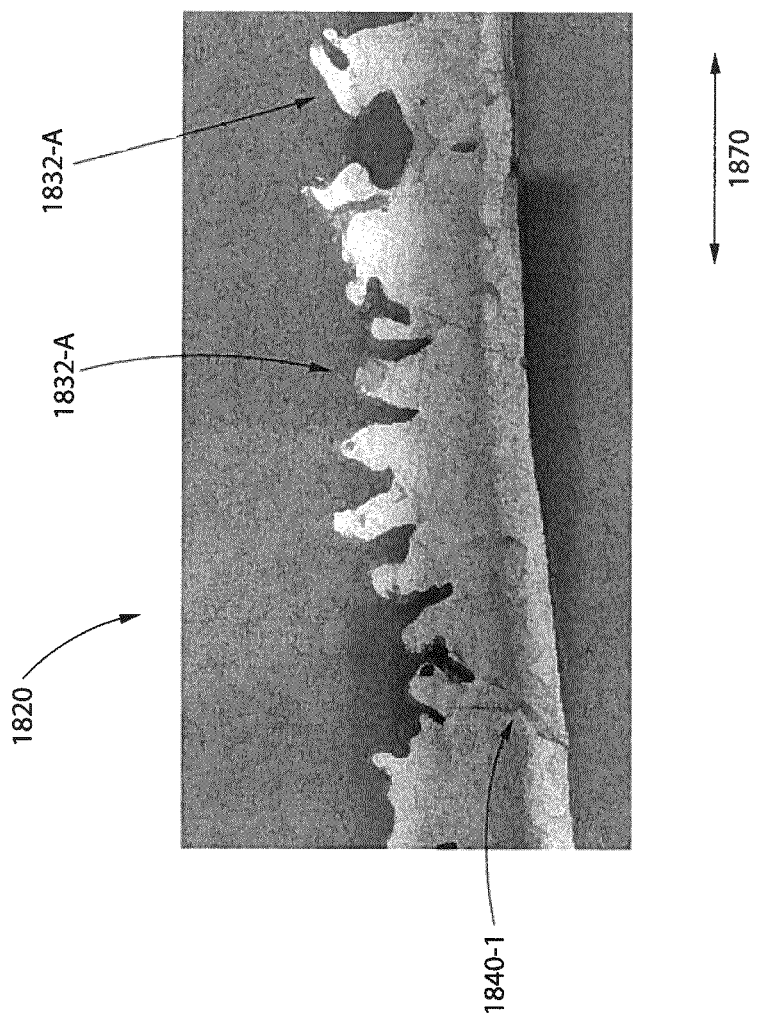
FIG. 16B is a microscopic photograph of a cross-section of an activated laminate with micro-texture of the present disclosure, in a contracted state.

FIG. 16B is a microscopic photograph of a cross-section of an activated laminate 1820 with micro-texture of the present disclosure, cut in a primary direction 1870 along an attachment line 1840-1. FIG. 16B shows some close-up detail of shirrs 1832-A on the laminate 1820, with the shirrs 1832-A filled with an adhesive along the attachment line 1840-1.

Figure 17:
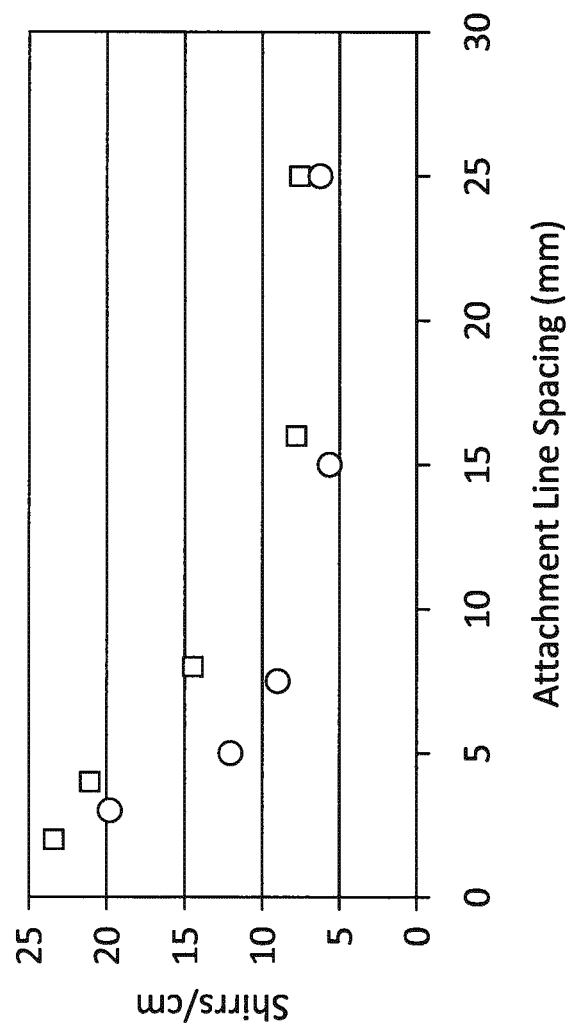
FIG. 17 is a graph illustrating number of shirrs per centimeter versus attachment line spacing for exemplary embodiments of an activated laminate with micro-texture of the present disclosure.

FIG. 17 is a graph illustrating number of shirrs per centimeter in a primary direction versus attachment line spacing in millimeters for exemplary embodiments of an activated laminate with micro-texture of the present disclosure. Without wishing to be bound by this theory, the graph of FIG. 17 appears to illustrate that the number of shirrs per centimeter is a function of attachment line spacing, with closely spaced attachment lines yielding a higher number of shirrs per distance and farther spaced attachment lines yielding a lower number of shirrs per distance. As a result, it appears that, for laminates of the present disclosure, the number of shirrs per centimeter can be controlled, at least in part, by selecting a particular spacing for attachment lines. In FIG. 17, the data points represented by squares correspond with the laminate of FIGS. 3A-3G, with the first layer being a sheet of film having elastic properties and the second layer 330-2 being a nonwoven laminated to a film having plastic properties, with attachment line spacings of 2 mm, 4 mm, 8 mm, 16 mm, and 25 mm. In FIG. 17, the data points represented by circles correspond with a variation of the laminate of FIGS. 3A-3G, with the first layer being a sheet of film having elastic properties and the second layer 330-2 being a nonwoven laminated to a film having plastic properties, with attachment line spacings of 3 mm, 5 mm, 7.5 mm, 15 mm, and 25 mm. The scale of FIG. 19 can be used to graphically determine exact values for the data points. The data shown in FIG. 19 was obtained by the Measurement Method Using Micro Computer Tomography, described herein.

Figure 18:
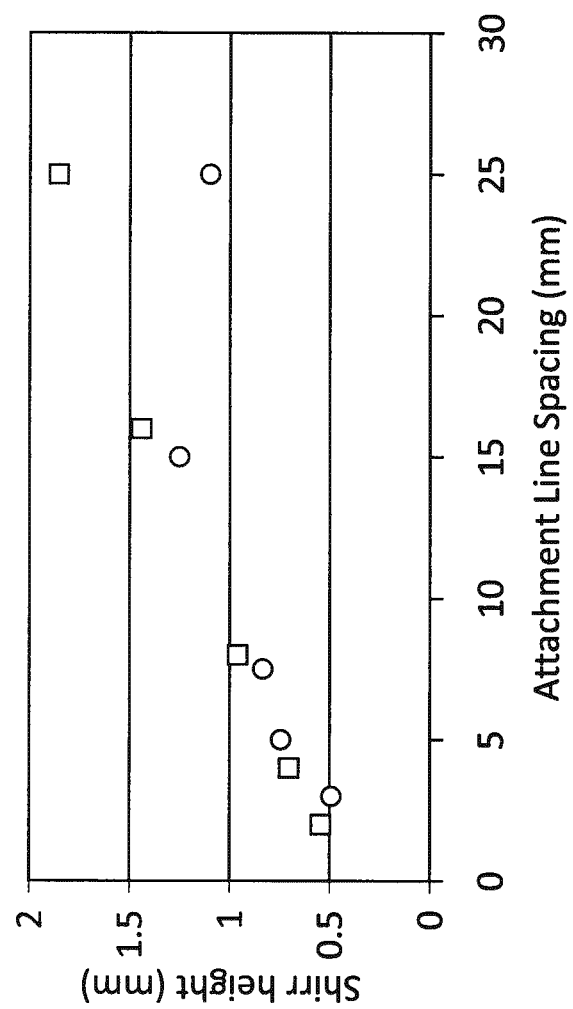
FIG. 18 is a graph illustrating shirr height versus attachment line spacing for exemplary embodiments of an activated laminate with micro-texture of the present disclosure.

FIG. 18 is a graph illustrating shirr height in millimeters versus attachment line spacing in millimeters for exemplary embodiments of an activated laminate with micro-texture of the present disclosure. The graph of FIG. 18 illustrates the fact that shirr height is likely a function of attachment line spacing, with closely spaced attachment lines yielding a shorter shirrs and farther spaced attachment lines yielding taller shirrs. In FIG. 18, the data points represented by squares correspond with the laminate of FIGS. 3A-3G, with the first layer being a sheet of film having elastic properties and the second layer 330-2 being a nonwoven laminated to a film having plastic properties, with attachment line spacings of 2 mm, 4 mm, 8 mm, 16 mm, and 25 mm. In FIG. 18, the data points represented by circles correspond with a variation of the laminate of FIGS. 3A-3G, with the first layer being a sheet of film having elastic properties and the second layer 330-2 being a nonwoven laminated to a film having plastic properties, with attachment line spacings of 3 mm, 5 mm, 7.5 mm, 15 mm, and 25 mm. The scale of FIG. 18 can be used to graphically determine exact values for the data points. The data shown in FIG. 18 was obtained by the Measurement Method Using Micro Computer Tomography, described herein.

Hysteresis Test

The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) to 25.4 mm.

4. Place the sample in the flat surface of the jaws such that the direction of interest is parallel to the gauge length direction. Mount the sample in the upper grip, let the sample hang slack, then close the lower grip. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

5(a). First cycle loading: Pull the sample to 200% strain at a constant cross head speed of 100 mm/min. Report the stretched sample length between the jaws as $l_{max}$.

5(b). First cycle unloading: Hold the sample at 200% strain for 30 seconds and then return the crosshead to its starting position (0% strain or initial sample length, lini) at a constant cross head speed of 100 mm/min. Hold the sample in the unstrained state for 60 seconds.

5(c). Second cycle loading: Pull the sample to 200% strain at a constant cross head speed of 100 mm/min.

5(d). Second cycle unload: Hold the sample at 200% strain for 30 seconds and then return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

1. Length of sample between the grips at a slack preload of 0.02 N/cm ($l_{ini}$) to the nearest 0.001 mm.

2. Length of sample between the grips on first cycle at the specified strain ($l_{max}$) to the nearest 0.001 mm.

3. Length of sample between the grips at a second cycle load force of 0.02 N/cm ($l_{ext}$) to the nearest 0.001 mm.

4. % set, which is defined as $(l_{ext}-l_{ini})/(l_{max}-l_{ini})*100\%$ to the nearest 0.01%.

The testing is repeated for six separate samples and the average and standard deviation reported.

Dimension Method

Various dimensions and ratios thereof are specified herein. Unless otherwise stated, each dimension is measured according to the following method. All testing is performed in a conditioned room maintained at about 23 C±2 C and about 50%±2% relative humidity. Herein, width and length of the specimen are a lateral width and longitudinal length as defined herein. Precondition specimens at about 23 C±2 C and about 50%±2% relative humidity for 2 hours prior to testing.

Prepare the article for testing as follows:

1. Lay the article on a substantially flat, horizontal surface.

2. Secure the article to the surface such that all process-induced contraction acting to forshorten the absorbent core assembly is pulled out. For example, a pre-contracted waistband applied to the article or elastics along the longitudinal edges of the article and/or the absorbent core assembled may forshorten the article laterally or respectively longitudinally, so any such process-induced contraction is pulled out. The article is secured to the flat, horizontal surface with clamps or adhesive tape capable of holding the absorbent core assembly with process-induced contraction pulled out.

3. Identify points between which widths and/or lengths of each attachment region, the absorbent core assembly, any unattached areas, and the article are to be measured, per definitions contained herein. This includes defining the hip region.

4. Measure each needed dimension to the nearest 1 mm using a steel ruler traceable to NIST.

5. Calculate any needed ratios as follows: Ratio=100%×[First Measurement/Second Measurement].

Measurement Method Using Micro Computer Tomography

Micro computer tomography can be used, as described below, to measure the number of shirrs per centimeter and the shirr height in activated laminates of the present disclosure. This method is only intended for measuring a mechanically activated laminate between two parallel and linear lines of attachment that attach a first to a second layer, as described herein. This method can be used for laminates such as these, that also include additional layers.

First, cut a round sample of the laminate material to be tested, with each sample approximately 36 mm in diameter.

Second, position the sample obtained from step one for scanning with first layer on the bottom, facing downward, and the second layer on the top, facing upward. For stable positioning, the bottom of the sample can be adhesively mounted onto a positioning surface, using double-sided adhesive foam. The sample should be undeformed, with the top and the sides of the sample left open to the air and unobstructed. Once mounted, the sample should lie substantially flat without significant wrinkles. If the sample does not lie flat, then shim material may be added under portions of the sample, for extra support. If the sample still does not lie flat, then it may be turned over so the second layer is on the bottom and the first layer is on the top.

Third, scan the positioned sample from step two with a micro-computer tomography system, such as µCT 40, ID#4286, serial #07030700, available from Scanco Medical AG of Wayne, Pa., USA. For this system, use the following scanning parameters: high resolution (1000 projections per 180 degrees) x-ray tube set for a current of 110-180 µA and a peak energy of 35 kVp, 300 millisecond integration time, and a frame averaging of 10. Scan with a slice increment of 18 µm. For samples of the size described herein, this may require a scanning time of several hours. For other systems, use equivalent settings.

Fourth, process the scan data from step three. Use each slice (consisting of 1000 projections) to reconstruct the image in a 2048×2048 pixel matrix, with a pixel resolution of 18 μm. Import the scan data into visualization software. For example, for reconstructed data from the Scanco Medical machine (described above), convert the data into an .AVW file and import the data into Avizo visualization software (versions 6.0 or higher, offered by Visualization Sciences Group) using a MATLAB script.

Fifth, align the scanned image data of the laminate from step four with each axis in the visualization space. This may require manual rotation, as follows. For the Z-axis, look at the XY plane of an orthoslice and rotate the data/image in small increments around the Z-axis until the lines of attachment in the laminate align with the Y-axis at the edge of the viewing area. As an example, in Avizo, apply the rotation transformation to all voxels using the standard Apply Transform command Check the results by taking a YZ orthoslice of the rotated data/image, viewing it as a straight line from the XY perspective, and checking for alignment with a line of attachment. If the orthoslice is closely aligned with the attachment line, then the rotation is complete. If not, then repeat the manual rotation step to improve the alignment. Repeat this procedure for the X and Y axes. At the end of the rotation step, the secondary direction of the laminate should coincide with the X axis, the primary direction of the laminate should coincide with the Y axis, and the tertiary direction of the laminate should coincide with the Z axis. As a result, the lines of attachment should line in the XY plane and should be oriented in the Y direction.

Sixth, use the rotated scan data from step five to make measurements of the laminate in the visualization software.

Define a rectangular volume of interest for the measurement. The top of the volume is in an XY plane and is defined by the outermost extent of the top of the shirrs of the second layer (disposed away from the first layer). The bottom of the volume defined is in an XY plane and is defined by the innermost extent of the bottom of the shirrs of the second layer (disposed toward the first layer). The left and right sides of the volume are each in a YZ plane and are defined by aligning the two sides on two adjacent lines of attachment in the laminate. The front and back sides of the volume are each in an XZ plane and are defined by the area of interest between the lines of attachment and in the Y axis direction.

Next, create an image for counting shirr crossings. Define a slicing plane within the volume of interest. The slicing plane is an XY plane, parallel to and midway between the top and the bottom of the volume. Take an orthoslice of the scan data at the slicing plane to create an image of the cross-sections of the shirrs of the second layer. In the image, the cross-sections of the shirrs appear wherever the shirrs cross the slicing plane. Define a reference line within the slicing plane. The reference line is oriented in the Y direction, parallel to the lines of attachment. Determine the overall length of the reference line in centimeters, from the front of the volume to the back of the volume. Make the reference line visible within the image of the cross-sections.

Next, determine the number of shirrs per centimeter. Using the image created from the slicing plane, manually count the number of intersections between shirr crossings and the reference line, along the reference line. Since there are two intersections for each shirr, divide the number of intersections along the reference line by two to obtain the number of shirrs along the reference line. Divide the number of shirrs along the reference line by the overall length of the reference line to obtain the number of shirrs per centimeter.

Next, determine the shirr height. In the Z direction, measure the overall distance between the top and the bottom of the volume of interest.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laminate, comprising:
   a primary direction;
   a secondary direction that is perpendicular to the primary direction;
   a first layer having, in the primary direction, a first extensibility and a first elasticity with a first set;
   a second layer having, in the primary direction, a second extensibility and a second elasticity with a second set that is greater than the first set;
   a first attachment line;
   wherein the first layer is attached to the second layer only by a first attachment area, and wherein the first attachment area is primarily formed by the first attachment line; and
   wherein the laminate has, in the primary direction, a laminate extensibility and a laminate elasticity with a laminate set;
   a plurality of shirrs in the second layer, wherein each of the shirrs is substantially parallel with the secondary direction; and
   a plurality of corrugations in the first layer, wherein each of the corrugations is substantially parallel with the primary direction.

2. The laminate of claim 1, wherein:
   the first attachment line is included in a plurality of first attachments lines, wherein each of the first attachment lines is oriented in a direction of orientation that is substantially parallel with the primary direction; and
   the first attachment area is primarily formed by the first attachment lines.

3. The laminate of claim 2, wherein each of the first attachment lines is a substantially continuous line.

4. The laminate of claim 2, wherein each of the first attachment lines is a line of adhesive.

5. The laminate of claim 2, wherein the plurality of first attachment lines has at least three lines.

6. The laminate of claim 2, wherein the plurality of first attachment lines has a uniform spacing.

7. The laminate of claim 2, wherein adjacent lines in the plurality of first attachment lines are spaced apart by a distance that is greater than or equal to two millimeters.

8. The laminate of claim 2, wherein each of the first attachment lines has a line width less than or equal to one millimeter.

9. The laminate of claim 1, wherein the laminate is in the form of a band with an overall length in a longitudinal direction and an overall width in a lateral direction, and wherein the overall length is substantially greater than the overall width.

10. The laminate of claim 9, wherein the primary direction is parallel with the longitudinal direction.

11. The laminate of claim 1, wherein the first layer is a film.

12. The laminate of claim 1, wherein the first set is less than or equal to 20% when measured using a Hysteresis Test.

13. The laminate of claim 1, wherein the second layer is a laminate formed by a film and nonwoven.

14. The laminate of claim 1, wherein the second set is greater than or equal to 50% when measured using a Hysteresis Test.

15. The laminate of claim 1, wherein substantially all of the first attachment area is formed by the first attachment line.

16. The laminate of claim 1, wherein the first layer is attached to the second layer by an attachment with an overall peel strength and substantially all of the overall peel strength is provided by the first attachment line.

17. The laminate of claim 1, wherein the laminate extensibility is greater than or equal to 50%.

18. The laminate of claim 1, wherein the laminate is in the form of a band with an overall length in a longitudinal direction and an overall width in a lateral direction, wherein the overall length is substantially greater than the overall width, and wherein the overall width is less than or equal to 20 millimeters.

19. The laminate of claim 1, wherein the second layer has been incrementally stretched in the primary direction.

20. The laminate of claim 19, wherein the shirrs are spaced such that there are at least eight shirrs per centimeter.

21. The laminate of claim 19, wherein each of the shirrs has an overall height that is less than or about equal to 2.0 millimeters.

22. The laminate of claim 19, wherein each of the corrugations has an overall height that is greater than or equal to 1.0 millimeter.

23. A disposable wearable absorbent article, comprising the laminate of claim 1.

24. The article of claim 23, comprising a front waistband formed by the laminate.

25. The article of claim 24, comprising a rear waistband formed by the laminate.

26. The laminate of claim 1, wherein:
a third layer having, in the primary direction, a third extensibility and a third elasticity with a third set that is greater than the first set; and
a second attachment line;
wherein the first layer is attached to the third layer only by a second attachment area, and the second attachment area is primarily formed by the second attachment line.

27. The laminate of claim 26, wherein the third layer is a film.

28. The laminate of claim 26, wherein the third layer is a nonwoven.

29. The laminate of claim 1, wherein the first and second layers are incrementally stretched in the primary direction.

30. A method of making a laminate, the method comprising:
providing a first layer having, in a primary direction, a first extensibility and a first elasticity with a first set;
providing a second layer having, in the primary direction, a second extensibility and a second elasticity with a second set that is greater than the first set;
attaching the first layer to the second layer by a first attachment area, primarily formed by a first attachment line to form an intermediate laminate;
forming a plurality of corrugations in the first layer in a direction substantially parallel with the primary direction;
forming a plurality of shirrs in the second layer in a direction substantially parallel with the secondary direction; and
incrementally stretching the intermediate laminate in the primary direction to form the plurality of corrugations and the plurality of shirrs.

31. The method of claim 30, wherein the attaching comprises attaching the first layer to the second layer by a plurality of first attachments lines, wherein each of the first attachment lines is oriented in a direction of orientation that is substantially parallel with the primary direction, and wherein the first attachment area is primarily formed by the first attachment lines.

32. The method of claim 31, wherein the attaching comprises attaching the first layer to the second layer by the plurality of first attachments lines, and wherein each of the first attachment lines is a line of adhesive.

33. The method of claim 30, comprising incrementally stretching the intermediate laminate by mechanically activating the intermediate laminate in the primary direction to form the laminate.

34. The method of claim 30, comprising:
providing a third layer having, in the primary direction, a third extensibility and a third elasticity with a third set that is greater than the first set; and
attaching the first layer to the third layer by a second attachment area, primarily formed by a second attachment line to form the intermediate laminate.

35. A laminate, comprising:
a primary direction;
a secondary direction that is perpendicular to the primary direction;
a first layer having, in the primary direction, a first extensibility and a first elasticity with a first set;
a second layer having, in the primary direction, a second extensibility and a second elasticity with a second set that is greater than the first set;
a first attachment line formed by a line of adhesive;
wherein the first layer is attached to the second layer only by a first attachment area, and the first attachment area is primarily formed by the first attachment line; and
wherein the laminate has, in the primary direction, a laminate extensibility and a laminate elasticity with a laminate set;
a plurality of shirrs in the second layer, wherein each of the shirrs is substantially parallel with the secondary direction; and
a plurality of corrugations in the first layer, wherein each of the corrugations is substantially parallel with the primary direction;
wherein the first and second layers are incrementally stretched in the primary direction.

36. The laminate of claim 35, wherein the first and second layers comprise a film.

37. A disposable wearable absorbent article, comprising the laminate of claim 35.

38. The article of claim 37, comprising a front waistband formed by the laminate.

39. The article of claim 37, comprising a rear waistband formed by the laminate.

* * * * *